(12) United States Patent
Lai

(10) Patent No.: US 8,366,274 B2
(45) Date of Patent: *Feb. 5, 2013

(54) SUBJECTIVE REFRACTION METHOD AND DEVICE FOR CORRECTING LOW AND HIGHER ORDER ABERRATIONS

(76) Inventor: Shui T. Lai, Encinitas, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/763,186

(22) Filed: Apr. 19, 2010

(65) Prior Publication Data

US 2010/0265463 A1 Oct. 21, 2010

Related U.S. Application Data

(63) Continuation of application No. 11/675,079, filed on Feb. 14, 2007, now Pat. No. 7,699,471.

(60) Provisional application No. 60/773,758, filed on Feb. 14, 2006.

(51) Int. Cl.
*A61B 3/02* (2006.01)
*A61B 3/00* (2006.01)

(52) U.S. Cl. ......... 351/222; 351/223; 351/243; 351/246

(58) Field of Classification Search ........... 351/222–246
See application file for complete search history.

(56) References Cited

U.S. PATENT DOCUMENTS

| | | | |
|---|---|---|---|
| 6,050,687 A | 4/2000 | Bille et al. | |
| 6,155,684 A | 12/2000 | Bille et al. | |
| 6,761,454 B2 * | 7/2004 | Lai et al. ....................... | 351/216 |
| 2002/0140902 A1 | 10/2002 | Guirao et al. | |
| 2003/0053031 A1 | 3/2003 | Wirth | |
| 2004/0100619 A1 | 5/2004 | Olivier et al. | |
| 2010/0265463 A1 | 10/2010 | Lai | |
| 2012/0169998 A1 | 7/2012 | Lai | |

FOREIGN PATENT DOCUMENTS

| | | |
|---|---|---|
| EP | 2026693 A4 | 1/2010 |
| EP | 2020904 A4 | 1/2011 |
| EP | 2020904 B1 | 3/2012 |

(Continued)

OTHER PUBLICATIONS

EPO Communication regarding the transmission of the European search report, Supplementary European search report, European search opinion, for European patent application No. 07 75 7012.5, report dated Dec. 15, 2009, 12 Pages.

(Continued)

*Primary Examiner* — Dawayne A Pinkney
(74) *Attorney, Agent, or Firm* — Andrew V. Smith

(57) ABSTRACT

A subjective refraction technique uses a plane wave light source including substantially a point as a viewing target. The refraction method provide for a number of distinct identifiable end points. By finding such end points the process leads to an aberration-corrected vision. A defocus corrector assembly (DCA) includes a lens that is moveable along an optical axis between a patient's eye and the point light source for adjusting defocus power until the patient indicates that the blurry image has become a relatively focused line image. An astigmatism corrector assembly (ACA) which is capable of continuously variable in its amplitude is provided including a pair of astigmatism plates for adjusting astigmatism power and axis angle. The ACA is adjusted until the patient indicates that the line image has become a substantially round image. A reference marker provides displayed items including a sweep line overlapping at the point source and having an orientation which is adjustable. The patient may subjectively control the sweep angle of the sweep line and indicate that the sweep line is aligned with the sharp line image of the point source, thereby providing axis angle data of astigmatism errors of the patient's eye.

17 Claims, 9 Drawing Sheets

FOREIGN PATENT DOCUMENTS

| | | |
|---|---|---|
| EP | 2468174 A1 | 6/2012 |
| WO | 98/27863 A1 | 7/1998 |
| WO | 03/034909 A2 | 5/2003 |
| WO | 2004/096014 A2 | 11/2004 |
| WO | 2005/079546 A2 | 9/2005 |
| WO | 2007/095596 A2 | 8/2007 |
| WO | 2008/088571 A2 | 7/2008 |

OTHER PUBLICATIONS

EPO Communication regarding the transmission of the European search report, Supplementary European search report, European search opinion, for European patent application No. 07 87 2213.9, report dated Dec. 22, 2010, 5 Pages.

* cited by examiner

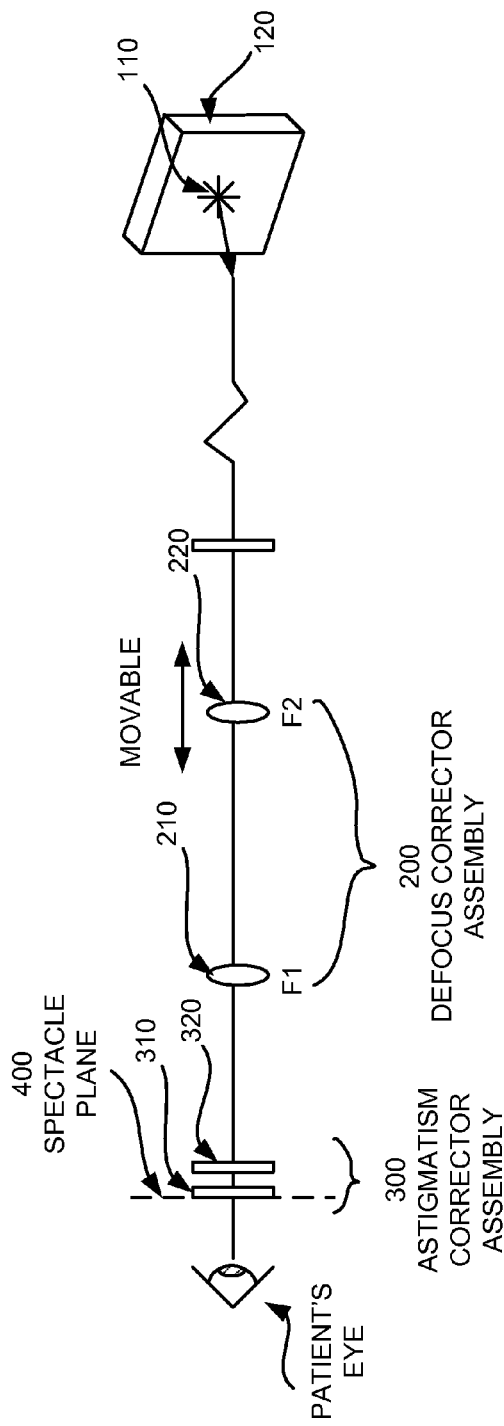
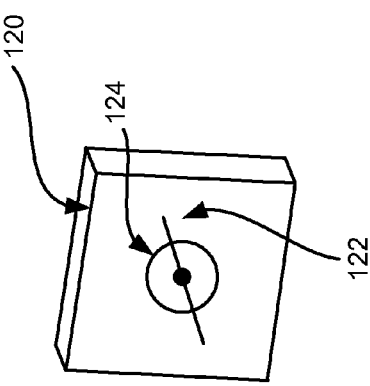
FIGURE 1A
FIGURE 1B

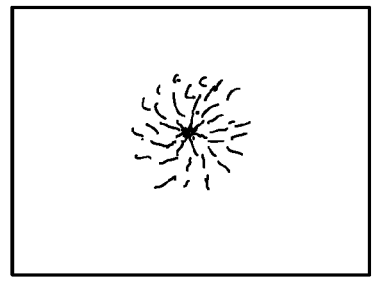
FIGURE 8A
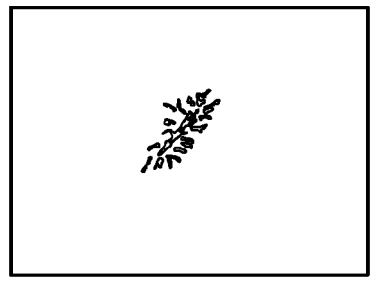 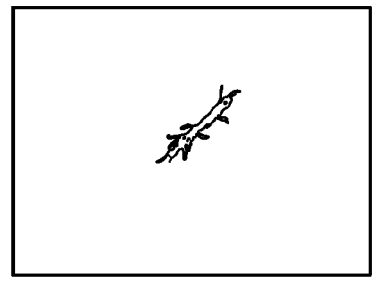
FIGURE 8B          FIGURE 8C
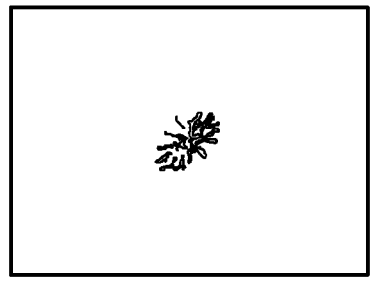 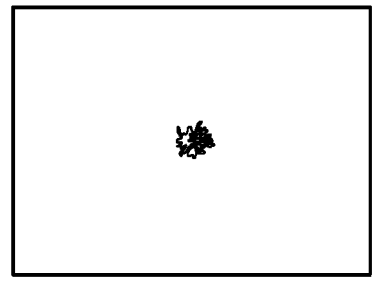
FIGURE 8D          FIGURE 8E
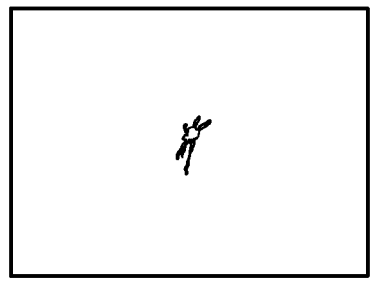 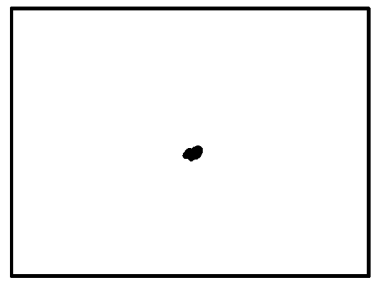
FIGURE 8F          FIGURE 8G

SUBJECTIVE REFRACTION METHOD AND DEVICE FOR CORRECTING LOW AND HIGHER ORDER ABERRATIONS

PRIORITY

This application is a Continuation of U.S. patent application Ser. No. 11/675,079, filed Feb. 14, 2007, now U.S. Pat. No. 60/773,758, which claims the benefit of priority to U.S. provisional patent application No. 60/773,758, filed Feb. 14, 2006, which is hereby incorporated by reference.

BACKGROUND

Subjective Refraction Methods

Most optometrists and ophthalmologists use a phoropter to measure subjective refraction, and use an eye chart, typically a Snellen chart, as the viewing target. During the examination, the administrator seeks oral indication from the patient, to choose which one of the two lens-settings provides better acuity, with which the patient is able to read more letters. However, being able to recognize a letter, therefore, being able to read it, is quite different from seeing the letter sharp and crisp. Oftentimes the patient has difficulty deciding which one of the two choices 1 or 2 is "better". This act of making a decision may in fact cause anxiety in some patients, since the answers ultimately will affect the prescription of his/her eyeglasses, and he/she is going to stay with that decision for the next couple of years. In the case of determining the cylindrical axis, the patient finds a point of "equally" blurred images. This is in principle an inferior method of finding the best image as the end point of a measurement.

The Snellen eye chart used in the refraction procedure is preferred in most practices because it can arrive at a spectacles prescription relatively quickly. Other types of eye charts such as Landolt-C eye chart, or contrast sensitivity measurement charts are preferred in research study that involves more precise quantification of visual function. Since these charts are used to arrive at the threshold point, measurements have to be repeated for accuracy, and in the case of contrast sensitivity measurement, repeated also for each of the selected spatial frequencies. So far, there is no single eye chart that can be used to assess all the key characteristics of visual function that can satisfy the desire to have more accurate spectacle prescriptions that maximize the quality of vision.

Limitation of Phoropter Refraction

Phoropter refraction is convenient and generally satisfactory. However, the redo rate (patient rejection of prescription) is still in the 5% range. More importantly, most eye care professionals make no effort to determine the best acuity setting for the patient, since that process is much more time consuming and worse still, the final prescription may be erroneous due to accommodation by the patient, causing an over correction condition, resulting in headaches, and dizziness. It is desired to provide a refraction method that does not compromise the highest quality of vision with expediency, and a method that takes less time than that of using a current phoropter.

Phoropter refraction methods can typically have a limited value when it comes to resolving patient complaints of nighttime driving problem, glares, and starbursts. It offers no solution nor explanation, and no quantification of how sharp or blurry a letter image on an eye chart may be, because a patient can guess what the letter is even when it is blurry. Therefore, Snellen refraction is imperfect, i.e., someone's 20/20 with blurry letters is far different from one seeing clear and sharp letters. It is desired to provide a device and method with which an eye-care practitioner can relate, such that he or she can explain and demonstrate based on experience with the patient's vision complaints, and offer a solution to reduce or eliminate the problem.

Objective Refraction Methods

Most autorefractors, including most of the recent wavefront aberrometers, use internal targets, whether it is an image of a balloon at the end of a roadway, or a spider web pattern or concentric ring patterns. Their main function is to "relax" the patient's accommodation and to set a condition for taking a measurement of the optics of the patient's eye. These objective measurements have common problems. First, they do not account for interpretational processing that takes place in the brain, and that transforms a retinal image to a perceptional image. Second, there are problems with instrument myopia, that is, a patient can accommodate because he or she knows they are looking inside a small box, not at a distant object.

Hence it is desired to provide a method of refraction for a patient to his maximized visual acuity without the disadvantage of over correction, or accommodation, and to provide a method that can better quantify a subjective quality of vision, other than using a Snellen chart or other such type of eye chart.

Limitation of Current Wavefront Correction of the Higher Order Aberrations of the Eye Since the introduction of wavefront (WF) aberrometers in refractive surgery, both ophthalmologists and optometrists have become aware of the effect on the vision of the higher order aberrations. The higher order aberrations are defined herein as those describable by Zernike polynomials or Fourier series beyond the second order Zernike polynomials, namely the defocus, astigmatism and axis. Partial wavefront correction of only the spherical aberration (Zernike Z(4,0) term) can be incorporated into commercial products. Technis intraocular lenses (IOL) by Advanced Medical Optics (AMO) correct a fixed amount of spherical aberration. Wavefront guided LASIK offered by VISX (AMO), Bausch and Lomb, and Alcon Labs, all attempt to cancel entire Higher Order Aberrations (HOA) of the eye by re-shaping the anterior cornea. Surgery is typically costly, and irreversible. The tissue healing process is highly dependent on the individual, and is unpredictable. The hyperplastic healing reaction easily erases most if not all intended WF correction profile. The WF guided LASIK surgery outcomes so far have not been optimal. Its current goal is not to induce any more HOA than that before the surgery, rather than achieving the grand objective of eliminating the HOA all together.

Recently, Ophthonix has developed wavefront-guided eyeglasses, by incorporating wavefront correction in lenses of eyeglasses. However, it is recognized herein that neutralizing HOA involves a wavefront retardation profile, which differs significantly from the HOA of the eye. The peaks and valleys of the WF correction on the lens would align with the HOA of the eye better than a fraction of a mm laterally at the spectacle plane to provide desired benefits of improvement in vision quality. Therefore, the useful range of the glazing angle in a WF guided spectacle lens is narrow. Misalignment causes more serious distortions, much worse than that without the HOA correction.

Furthermore, Ophthonix and WF guided LASIK, all use the objectively measured WF data from an aberrometer while assuming that a 100% WF aberration correction is best for the patient. In so doing, the participation of the human brain to process the retinal stimuli, and determine the perceived image quality is ignored.

Therefore, it is advantageous to provide a method of correcting HOA that is non-surgical, safe, reversible and low cost, that does not induce more HOA when the patient looks at various glaze angles, and/or that incorporates the patient's subjective vision system including the brain's image processing.

Disadvantages of Click-and-Measure Methods

With most auto-refractor or wavefront aberrometers, the measurement that determines the patient's refraction errors is taken with a single click. That is, the measurement is objective, with no participation of the patient's image perception formation process from the retina to the brain. The patient's optics are frozen at the moment the measurement is taken. The patient may be temporarily distracted, looking off-axis, or experiencing instrument myopia. These factors can cause erroneous results, and a less than ideal refraction. Subjective refraction significantly eliminates the drawbacks of click-and-measure methods.

SUMMARY OF THE INVENTION

A subjective refraction method is provided for generating a prescription for one or more corrective lenses for a patient. A patient's eye is disposed in a substantially fixed position. A point light source is provided including substantially plane wave wavefronts as a viewing target. A blurry image of the point light source is formed at the patient's eye through an optical assembly. This image includes a refractive error or optical aberration, or both, of the patient's eye. One or more optics of the optical assembly, that are continuously disposed along an optical path between the point light source and the patient's eye, are adjusted until the patient indicates that the point light source has become substantially focused such that said refractive error or optical aberration, or both, of the image are substantially reduced. A prescription is determined for a corrective lens for the patient's eye based on known parameters of the optical assembly and on at least one adjusted position or orientation, or both, of the one or more optics of the optical assembly.

The optical assembly may include a defocus corrector assembly (DCA), and the adjusting may include moving at least one lens of the DCA along the optical path until the patient indicates that the blurry image has become a linear image. By linear image, it is meant that the blurry image has been made to be more linear than before the adjusting, and not necessarily to form a neat, clean line. The patient will preferably indicate the most linear image that he or she observes in the course of the adjusting (see example of FIGS. 8A-8B going from blurry image of point light source to linear image). The DCA may include a pair of achromatic lenses disposed along the optical path including a fixed lens having a back focal length at a spectacle plane or equivalent spectacle plane of the patient's eye and a movable lens between the fixed lens and the point light source.

The optical assembly may also include an astigmatism corrector assembly (ACA), and the adjusting may include rotating at least one lens of the ACA until the patient indicates that the line image has become a point image. By point image, it is meant that the linear image of the initially blurry image is now reduced in its long dimension, preferably by adjusting the ACA (see exemplary change of linear image to round or oblong shape at FIGS. 8B and 8D). The ACA may include a pair of astigmatism wave plates disposed approximately at a spectacle plane or equivalent spectacle plane of the patient's eye. The adjusting of optics may include adjusting different optics than a DCA or ACA as described herein to adjust the blurry image to a more linear image and then to reduce the long dimension of the linear image to a round or oblong shape. In a preferred embodiment, the blurry image becomes very nearly a line, and the line becomes very nearly a round, symmetrical point.

A quality vision marker (QVM) may be provided including one or more display items overlapping with or proximate to the point light source. At least one of the display items may be adjusted relative to the line image or point image, or both. The at least one display item may include a sweep line, and the adjusting of the display item may include overlapping the sweep line with the line image to determine an axis angle. The at least one display item may include a circle, or multiple circles, one line or multiple lines, a single point source, or multiple point sources arranged along a line or a circle, or combinations thereof and the adjusting of the display item may include centering the circle at the point image, changing the spot size or the dimensions of the point source, or the brightness intensity of the point source or sources, or combinations thereof.

The prescription may be adjusted for higher order aberrations (HOA) by:
(i) reducing a brightness or size, or both, of the point light source;
(ii) generating a point or a ring pattern of multiple point sources, or both, at the QVM; and
(iii) adjusting the defocus power and astigmatism power by tilting an ACA component to adjust ACA amplitude or its optical axis, or the defocus DCA, or combinations thereof, thereby minimize HOA.

A defocus power of the DCA and ACA may be adjusted within predetermined limits, including:
(i) searching for a residual line image of the point light source along the sweep line orientation;
(ii) reducing a diopter power of the DCA to attain a least minus power and at which a sharp line image is formed at the point source; and
(iii) increasing ACA diopter power to reduce the line image to a small and substantially round point image.

The defocus power of the DCA and ACA may be differently adjusted within predetermined limits, including:
(i) searching for a residual line image of the point light source perpendicular to the sweep line orientation;
(ii) reducing diopter power of the DCA to attain the least minus power and at which a sharp line image is formed at the point source; and
(iii) decreasing ACA diopter power to reduce the line image to a small and substantially round point image.

A display may be provided as a second viewing target centered approximately at the location of the point light source. The display may provide one or more viewing items including a sweep line. An orientation of the sweep line may be adjusted until the patient indicates that the sweep line has become substantially aligned with an orientation of the line image of the point source.

The optical assembly may include an astigmatism corrector assembly (ACA) including a pair of astigmatism wave plates, and the adjusting may include rotating an optical axis of the ACA to an orientation substantially perpendicular to the orientation of the sweep line. An amplitude of astigmatism correction may be increased by changing a subtended angle of the astigmatism wave plates until the line image of the point is reduced to a substantially round image.

One or more corrective lenses is/are also provided having a prescription generated by the subjective refraction method set forth above and/or below herein.

A further subjective refraction method is provided for generating a prescription for one or more corrective lenses. A collimated light beam is provided including substantially plane wave wavefronts. The plane wave wavefronts are projected into a patient's eye. An image of the wavefronts is formed at the patient's retina through an optical assembly in the light path including a defocus corrector assembly (DCA) or astigmatism corrector assembly (ACA), or both. The image initially includes refractive errors or optical aberrations, or both, of the patient's eye. While subjectively observing a shape of the image, the patient is instructed to search for and indicate at least one end point by adjusting the DCA or the ACA, or both. A prescription is determined for a corrective lens for the patient's eye based on known parameters of the optical assembly and on the adjusting of the DCA or the ACA, or both.

The at least one end point may include a line image which is observed by the patient to be at its sharpest or at its longest, or both.

A subjective refraction method for revising a prescription for one or more corrective lenses to correct higher order aberrations (HOA) of the eye of a patient is also provided. A point light source including substantially collimated plane wave wavefronts is provided at the patient's eye as a first viewing target. A low order prescription is input to a defocus corrector assembly (DCA) and an astigmatism corrector assembly (ACA) that are disposed along an optical path between the point light source and the eye of the patient, including setting an optical axis of the ACA to a cylindrical axis of the low order prescription. A brightness of the light source is adjusted to avoid eye saturation. The patient is instructed to observe one or more higher order aberration features around a point image of the plane wave. An angle of the optical axis or the power of the ACA or the power of the DCA, or combinations thereof, are adjusted to reduce the one or more higher order aberration features around the point source image. The prescription is revised based on known parameters of the ACA or DCA or both and on the adjusting.

The size or the dimensions of the point source may be controlled or adjusted to provide high acuity vision of better than 20/15. A display may be provided as a second viewing target. The display may provide one or more rings centered approximately at the location of the point light source, or multiple circles, one line or multiple lines, a single point source, or multiple point sources arranged along one or more lines or circles, or combinations thereof. The diameter of at least one ring may be adjusted to provide a reference marker for the extent of the HOA. The brightness of one or more point sources or a size of one or more point sources, or both, may also be adjusted.

A subjective refraction apparatus is also provided for generating a prescription for one or more corrective lenses of a patient. A plane wave light source includes substantially a point light source as a viewing target. At least one input device is provided for the patient or for an examination administrator or both. An optical system is disposed along an optical axis between the point light source and the patient's eye which initially forms a blurry image of the point light source at the patient's eye. The optical system includes a defocus corrector assembly (DCA) including a fixed lens and a lens that is movable along the optical axis using the at least one input device for adjusting defocus power until the patient indicates that the blurry image has become a relatively sharp line image. An astigmatism corrector assembly (ACA) includes a pair of astigmatism wave plates that are relatively adjustable along its z-axis (perpendicular to the wave plate surface). One may use the at least one input device for adjusting the DCA or the ACA, or both, for astigmatism power or axis angle, or both, until the patient indicates that the line image has become a substantially round image.

A reference marker provides a sweep line overlapping at the point source and having an orientation which is adjustable using the at least one input device until the patient indicates that the sweep line is aligned with the sharp line image of the point source, thereby providing axis angle data of astigmatism errors of the patient's eye.

The plane wave light source may include a point source placed two meters or farther away from the patient and may have a diameter of two millimeters or less. The plane wave light source may include a substantially collimated light beam from a laser source that simulates a point source positioned two meters or farther away from the patient. A lens may cause an image of the point source to appear to the patient to be two meters or farther away.

Spectral contents of the light source may include white light, substantially blue light, substantially yellow light, or substantially red light.

The marker may provide a display pattern including one or more rings or parallel lines, a circle or multiple circles, one line or multiple lines, a single point source or multiple point sources arranged along one or more lines or circles, or combinations thereof.

Electrical or electronics hardware or computer programs, or combinations thereof, may be provided that perform individually or collectively one or more of the following tasks:

(i) drive movement of one or more optical elements in the DCA or ACA, or both, to change defocus or astigmatism power, or both;
(ii) display a location of an optical element;
(iii) convert a location or orientation reading, or both, to a refractive power in units of diopters;
(iv) collect data relating to adjustments to the DCA and ACA;
(v) set limits of movement range for the DCA or ACA or both to avoid over-correction;
(vi) automatically advance DCA or ACA refractive power, or both, when such task is requested; or
(vii) automatic align the ACA optical axis when such task is requested, or combinations thereof.

An astigmatism corrector assembly ACA is also provided, which is capable of a variable correction amplitude, or a variable axis angle, or both. It includes at least two wave plates, including a first and a second wave plate. The first and second wave plate may have a second order Zernike polynomial of pure astigmatism wavefront correction profile in a x-y plane $Z(2,2)$ or $Z(2,-2)$. The first and second wave plates may be mounted with their wavefront profile origins aligned along an axis (Z-axis), One or both of the wave plates may be angularly adjustable with respect to said Z-axis.

BRIEF DESCRIPTION OF THE DRAWINGS

FIG. 1A illustrates subjective refraction apparatus in accordance with an embodiment.

FIG. 1B illustrates a quality vision marker (QVM) including point light source in accordance with an embodiment.

FIG. 8A illustrates an initially blurry image of the point light source in accordance with an embodiment.

FIG. 8B illustrates the blurry image of FIG. 8A converging to a linear image.

FIG. 8C illustrates a most substantially focused linear image indicated by a patient, still with spokes of light rays around it, in accordance with an embodiment.

FIG. 8D illustrates the linear image of FIG. 8B being reduced in its long dimension and collapsing to form a round or oblong shape.

FIG. 8E illustrates an example of a most symmetric shape indicated by a patient in accordance with an embodiment.

FIG. 8F illustrates a focused point with starbursts as high order aberrations.

FIG. 8G illustrates the image of FIG. 8F corrected in accordance with an embodiment.

DETAILED DESCRIPTION OF PREFERRED EMBODIMENTS

Figure 1C:
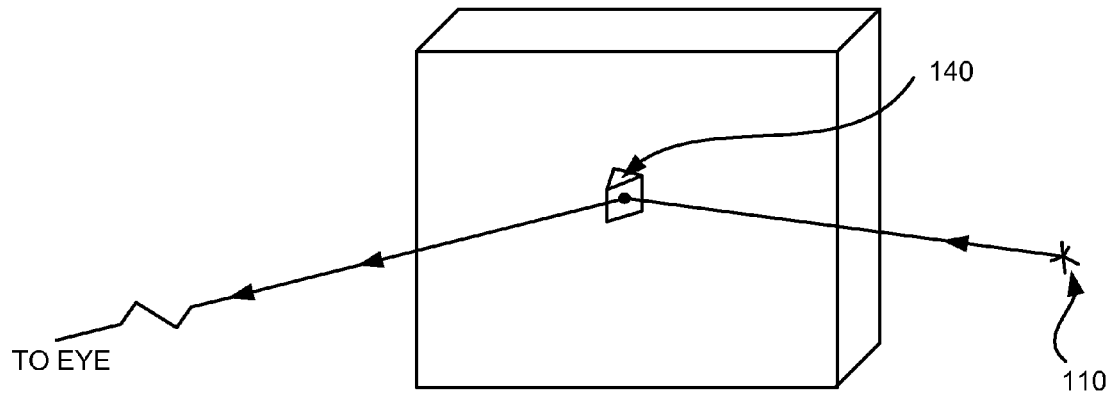
FIG. 1C illustrates a QVM with point light source reflected from the side in accordance with an alternative embodiment.

A subjective refraction method and a WF refraction device are provided that use defocus and astigmatism terms to correct both the second order (it is also referred to as the low order) and high order aberrations (sometime referred to as higher order, namely, third order and higher terms as described by Zernike polynomials). The spectacle prescription from the present refraction method is free from induced blur due to glazing at various angles.

The present refraction method provides a clear end point for the defocus. It also provides the axis angle of the astigmatism defects, and the optimal cylindrical angle that corrects the astigmatism. Furthermore, the present method enables the correction of HOA using defocus, astigmatism and axis, without inducing increases of HOA at various glazing angles. Furthermore, the device is capable of determining the least minus power point, not causing an over correction.

Furthermore, the refraction process takes less time than using phoropter refraction, and provides a high contrast sensitivity and visual acuity vision. It is refracted under white light, not limited by the monochromatic nature of the probe beam as in the case of most WF aberrometers.

As stated in the earlier discussion, the refraction methods using a phoropter, autorefractors, or wavefront aberrometers, are not all ideal, and have many disadvantages. The preferred embodiments include alternative refraction methods and devices that are subjective. The patient participates in arriving at the final refraction end point. A viewing target is presented unlike any of the eye charts used in the current refraction methods. The preferred target provides high degrees of discrimination for the patient to arrive at a final refraction point. Furthermore, a new refraction instrument is provided, as well as a new refraction method that arrives at a refraction prescription in less time and produces more reliable results without over-correction.

A preferred embodiment of the present refraction device is described as follows:

Plane Wave as a Refraction Target

The choice of a target used in a refraction measurement affects in a significant way the output parameters which are the intent of the measurement. Snellen charts, contrast sensitivity charts like sine gratings and Landolt c, have a specific objective and the outcome of the measurement depends entirely on the type of eye chart, and the accuracy and the specificity of the outcome measure depends on how the data are extracted from the patient. A target that provides clear and easily identified end points fares better in arriving at a more accurate prescription.

In a Shack-Hartmann wavefront aberrometer, a laser beam is incident into the eye to generate a small point source at the retina. However, the refractive errors of the patient's eye, including low order and higher order aberrations interact with the incident beam. This distorts the quality of the image at the retina, and low order errors displace the location of the beam. Therefore, the spot size and location of such light spot varies with the patient. The same aberrometer measures different types of wavefronts from patient to patient. The wavefront from this distorted light spot is used as the "reference wavefront" or the ideal wavefront, reflected back out of the eye. The resultant wavefront is then used to quantify aberrations of the entire optic system of the eye, through the pupil. The wavefront exiting the eye now contains aberrations of the eye double-passed, and is then captured and analyzed at a Shack-Hartmann sensor, which includes preferably a two dimensional lenslet array.

In a preferred embodiment, a subjective wavefront refraction method is provided. A substantially collimated beam includes substantially plane waves set to be incident upon a patient's eye. In this case, the quality of this reference wavefront may be controlled and made to be an undistorted plane wave, since it is prepared outside of the eye. If there is no refractive error, the patient will see a diffraction limited spot, or a tightly focused point image. However, if there is either low order and/or high order aberration(s) in the patient's eye, the patient would see a spread of light intensity distribution, which can be approximated by the Point Spread Function (PSF) of the aberrated eye as limited by the pupil opening. Therefore, a method in accordance with certain embodiments uses a substantially ideal plane wave to probe the refractive errors of an eye. The patient subjectively minimizes his or her own refractive errors while observing the image of the plane wave. This refraction method also provides instructions for the patient to arrive at a final prescription, with clearly defined end points, while observing and minimizing a spatial light distribution of a plane wave.

A point light source provides for a discriminating target for the patient. The point light source can be provided by a collimated beam from a laser source, or an incandescent or other uncollimated point source behind a small aperture, or a LED, or a small LCD or other display items is illustrated schematically as 110 in FIG. 1(*a*). The point light source can be generally any relatively small, arbitrary shape, although it is preferably round. The point light source can also be a dark point surrounded by lighter pixels, particularly if a display is used. In the case of a point source, it is to be preferably placed at about 2-6 meters or farther from the patient to provide a substantially collimated plane wave. Preferably the source is placed at a perceivable distance of more than 2 meters away from the patient's eye. It can be, for example, a white light LED, or the end of a fiber optic cable with white light focused at the other end, or a pinhole and a white light source focused through the pinhole, or a point image generated at a high brightness monitor such as a plasma screen, LCD, or Digital Light Processing (DLP) monitor screen. Other methods may also be used to generate a collimated plane wave, including use of a point source at or near the focal point of a condenser lens. Beam expansion and collimation techniques may also be used to expand the beam cross-section to over-fill a patient's pupil.

The point light source preferably has sufficiently small dimensions, e.g., of the order of 2 mm or less in its cross section, and that is preferably round in shape, and that can be regarded substantially as a "point" at a sufficiently far away distance, e.g., about 2-6 meters. Preferably the source is placed at a perceivable distance of more than 2 meters away from the patient's eye. This distance is chosen to be consistent with other refraction prescription methods. Farther distances can also be used in the refraction. As discussed earlier, a collimated laser beam can also be used to provide the plane wave wavefront.

Alternatively, a lens can be used in front of a point source to cause the formation of an image of a point source to the patient, so that the point source appears to be at about 2 meters (perceivable distance) or farther away from the patient. In the following, a 6 meter distance is used as an example for the point source and it is to be understood that the point source can be placed at 2-6 meters, or farther away from the patient. For those skilled in the art, the location of the point light source from the patient's eye directly affects the correction defocus power. However, this can be accounted for once the distance of the point source to the patient is known, or fixed.

A computer monitor may also be used to replace a conventional eye chart, but the purpose would be simply electronically replacement a paper eye chart or a projected image from a slide, except the letter arrangement may be changed electronically to eliminate memorizing by a patient of a printed or a fixed slide eye chart, and the display presented to the patient may be the same as those letters or the Landol-C letters in the chart. This would be a substantially different way of using a monitor compared with certain embodiments described herein. Preferably the point source is a white light source. It is really somewhat of a disadvantage of WF aberrometers to be monochromatic. They depend on the wavelength of the probe laser wavelength used, which is typically at about 820 to 860 nm. It is advantageous to use the continuum visible spectrum in the range from about 400 to 750 nm which the photo-sensor of the retina is capable of responding to for forming color and image perception. Change of the white light to color light or adding a color filter to select certain spectral or color contents may also be done in certain embodiments, which may include substantially blue, yellow, or red color. White light has the advantage of the full color spectrum, and the subjective perception of the point source image therefore includes the chromatic aberration of the visual system and compensations in signal processing as perceived in the brain.

Quality Vision Marker (QVM)

Another component of the preferred refraction system is a Quality of Vision Marker (QVM), which is illustrated as 120 in FIG. 1(*a*). It includes a display (LCD monitor, for example) and a computer program that generates various display items. The QVM is useful to assist the patient to identify refraction error, including the identification of an axis of astigmatism. A monitor and some display items are illustrated in FIG. 1(*b*). One example of such display item is a radial sweep line with the center overlapping the point source. The sweep line 122 points from the origin of the coordinate, that is at the point source's location radially, or it can extend diametrically through the origin point, namely, when one arm of this line is pointing at 30 degrees, and the opposite end of the sweep is pointing at 210 degrees. A set of parallel lines can also be used in the sweep. The displayed items are typically overlapping with or proximate to the point light source.

In Box 520, a Quality of Vision Marker (QVM), which includes a LCD monitor along with items of image displayed on it, may be either placed at the point source as shown in FIG. 1(*a*), with the point source substantially at the center of the monitor, thereby the radial sweep line originates at the point source, and the ring pattern is concentric to the point source as well. Alternatively, the point source may be detached from the monitor, and in the place of the point source in FIG. 1, at the center of the monitor is a 45-degree mirror 140, and the point source placed farther down as shown in FIG. 1(*c*). This layout has the advantage of wiring and the bulk associated with the point source will not interfere with the display on the QVM monitor.

Alternatively, the QVM monitor may be placed off the direct beam path of the point source in FIG. 1(*a*). With a 45-degree window that is semi-transparent, with a partial (50%, for example) transmission, in the beam path and establishes a second path of the patient's line of sight towards the monitor, such that the patient sees both the QVM monitor and the point source target. This layout also eliminates blockings that may be caused by the wires of the point source.

In FIG. 1(*a*), a patient's eye is shown to look along the beam path of the point source, and the QVM monitor. The patient's head is properly restrained, with a headband (or a headrest) and a chin rest. Other method of keeping the head/eye position steady may also be used.

The QVM is also capable of generating rings, 124, which center at the point source, and whose radius can be varied with an input control. It also generates parallel lines, or any other display items that can enable patient communication with the examiner on the status of the patient's eye conditions. The QVM device can be a round disc with a straight line passing through the center. In this case, the disc is rotatable with respect to its center. Concentric markings and other parallel line marking are also provided. Light channels are provided to feed illumination light to the diagonal line, or lines, parallel lines or the rings, so that only the desired item is lighted for the patient. A subjective wavefront refraction method is described below detailing exemplary methods for using the QVM to estimate astigmatism axis error.

The intensity levels and the size or the dimensions of the point source, and those of the display items of the QVM are adjustable; via some touch keys, infrared or blue-tooth removal control, or other control means.

Figure 1D:
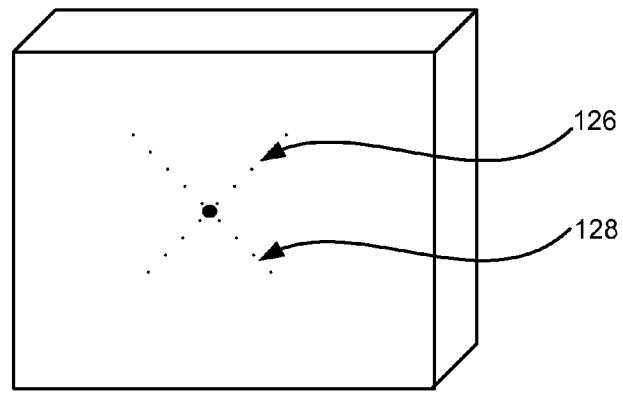
FIG. 1D illustrates a QVM with series of points arranged in two lines as display items around the point light source in accordance with an embodiment.

In an embodiment, multiple point sources may be presented. They can be physically focused spots or spots constructed to display in a LCD or DLP monitor. In FIG. 1(d) multiple points are constructed along a sweep line 126, instead of a solid sweep line as in FIG. 1(b), 122. Furthermore, multiple sweep lines can also be presented as shown in FIG. 1 (d), 126 and 128. As will be shown later, it is advantageous to arrange the sweep points 126 and 128 at 90 degrees. However, the angle of separation among the multiple lines sweeps may be at angles other than 90 degrees.

Figure 1E:
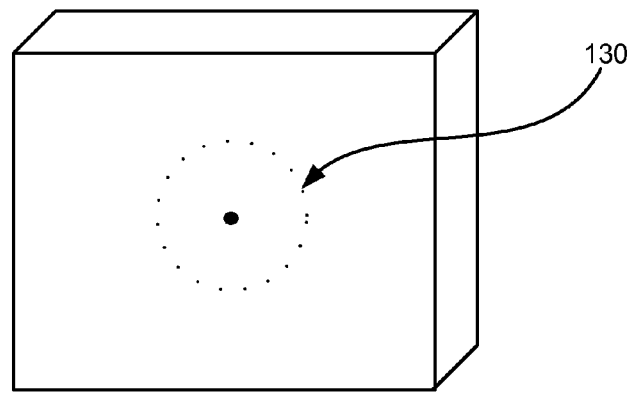
FIG. 1E illustrates a QVM with a series of points arranged in a circle as display items around the point light source in accordance with an embodiment.

In another embodiment, the multiple point sources may be arranged in a circle 130, as shown in FIG. 1(e). Multiple circles are optional. In addition to the patterns described above, points and lines can be arranged to form other patterns such as squares, ellipses, rectangles, other polygons such as triangles, or parallelepipeds. The spot size, its brightness and spots separation distance in lines 126, 128 or circle 130, or other patterns are adjustable to suit the purpose for the refraction procedures.

The refraction device also provides fixation for the patient's head. It may include a headband, a headrest, and/or chin rest, similar to those in most slip-lamp instruments, providing a rest position for patient's head and eye. Other method of keeping the head stationary may include a bite bar. Once the head position is stationary, the spectacle plane 400 of the eye is now known relative to the eye, which is about 12-15 mm from the apex of the patient's eye.

Defocus Corrector Assembly (DCA)

After the patient has kept his head stationary as described, the refraction starts with determining the defocus refractive errors. Defocus Corrector Assembly 200 is capable of providing a continuously variable power change at the spectacle plane of the patient's eye under examination. This is in contrast with the discrete incremental power change in a phoropter typically in 0.25 diopters steps. The present refraction method and device may include multiple or a series of lenses in smaller diopter power increments to be inserted in place of the DCA to accomplish the advantageous objective of finding the optimal refraction for the patient. For example, an instrument including lenses in 0.125 diopters increments, or in 0.0625 diopter increments may be used.

In the example illustrated at FIG. 1(a), the optical elements in the Defocus Corrector Assembly preferably include a pair of achromatic lenses 210, 220. Lens 210 has a focal lens F1, with a back focal length at the spectacle plane 410, and its position is preferably stationary. A second lens 220, has a focal length F2, and is positioned along the optical path of the patient's line of sight to the point source 110. Lens 220 is movable along the optical axis along the line of sight of the patient's view of the target point source. Depending on the location of lens 220 relative to lens 210, the Defocus Corrector Assembly produces either plus or minus lens powers at the patient's spectacle plane 400. The preferred range of defocus refractive power change is from +10 diopters to −12 diopters, and the range can be extended to +12 diopters to −20 diopters, or larger dioptric range if one desires. Alternatively, a series of spherical lenses may be used.

In one embodiment, the DCA is designed to optimize its field of view and minimize optical distortion on axis and off axis. The variable diopter range may be, for example, +8D to −10D. One may extend the useful diopter range of the instrument by placing a single additional lens at the patient's spectacle plane. In one example, so placing a +8D lens, the patient can be refracted up to an extended range of +16 D. Likewise one may extend the minus diopter range to −20 D with the insertion of one −10 D lens at the patient's spectacle plane. The extension method places no limitation on the field of view and substantially reduces the design requirement in the optics, demanding +18D to −20D all provided by lenses 210 and 220.

Astigmatism Corrector Assembly (ACA)

The astigmatism of the eye is preferably determined by using an Astigmatism Corrector Assembly 300, including pure astigmatism wave plate optical elements positioned near the spectacle plane of the patient. By pure astigmatism, it is meant the wavefront correction is to be described by either the Zernike functions Z(2,2), Z(2,-2) or combination thereof. Here and in the following, symbols of Zernike representation are used as adopted by the Optical Society of America, as described in Appendix one of "Customized Corneal Ablation: Quest for Super Vision" edited by MacRae, Krueger and Applegate, published by Slack in 2001, which is hereby incorporated by reference. Alternatively, it can also be positioned at an equivalent spectacle plane, which is produced by a relay lens system which may include a pair of lenses positioned at focal length separations from each other to produce a conjugated spectacle plane. The ACA is capable of providing continuously variable, pure astigmatism correction of the Zernike terms Z(2,2) and Z(2,-2). The astigmatism wave plate can be manufactured using CNC machining in an optical quality plastic plate or other type of substrates. Each of the optical elements are machined to provide an optical path difference (OPD) according to the shape of a Z(2,2) or Z(2,-2). This is an advantageous feature of the preferred refraction device. The preferred device goes beyond using cylindrical lenses mounted in a wheel. Cylindrical lens power also includes a component of defocus. Therefore, arriving at a final reading using cylindrical lenses involves adjusting a corresponding compensational change in the sphere component. This process can be tedious and can encourage accommodation and hence over-correction.

Using a modified notation of the Zernike Polynomials (without the normalization coefficients):

$$Z(2,+2,\theta)=r^2 \cos(2\theta) \quad (1)$$

$$\text{And } Z(2,-2,\theta)=r^2 \sin(2\theta)=r^2 \cos(90-2\theta)=Z(2,+2,\theta-45°) \quad (2)$$

where the third index within the bracket of the Zernike function designates the rotational angle of the astigmatism wave plate. Indeed Z(2,2) and Z(2,-2) terms are physically identical, except for the orientation of its optical axis being rotated by 45 degrees. If one desires an astigmatism correction range of 0 to 6 diopters, for example, the Astigmatism Corrector Assembly (ACA) may include two identical 3 diopter pure astigmatism wave plates. In the following it is shown that when these two plates have their axes aligned, it produces the maximum effect of 6 diopters of pure astigmatism, and when the angle subtended by the axes is 90 degrees relative to each other, it produces a total cancellation of each other's effect. Therefore, one may vary the amplitude of pure astigmatism by setting the angle subtended by the optical axes of two identical astigmatism wave plates:

$$\text{Variable } Z(2,+/-2)=Z(2,+2,\theta+\phi)+Z(2,+2,\theta-\phi) \quad (3)$$

Where angle φ is the subtended angle of each of the wave plate respect to initial axis combined unit ACA, therefore the total subtended angle between the two wave plates is 2φ. The initial axis of the combined unit is chosen to be at 90 degrees, since Z(2,+2) generates a negative cylinder lens at 90 degrees when a negative power sphere of half of its amplitude is added to it.

Starting with two Z(2,2) wave plates, optically aligned, one has the maximum astigmatism effects of 2Z(2,2).

Now one starts counter rotating the identical plates with an equal angle φ, $$Z(2,+2,\theta+\phi)+Z(2,+2,\theta-\phi)=2Z(2,+2,\theta)\cos(2\phi) \quad (4)$$

Therefore, maximum effect is at φ equal to zero, namely two plates are optically aligned, and minimum at φ equal 45 degrees. In this case, one can choose the optical axis of the combined unit to be at 90 degrees. Regardless of the value of counter rotating angles, the optical axis remains unchanged, the negative cylinder lens of equation (4) remains at 90 degrees when an appropriate amount of negative sphere is added to the combined unit. In application, one marks the 90 degree orientation as the optical axis of the combined unit in Equation (4), and the amplitude of the astigmatism decreases with increasing angles of φ. To provide another illustration, one may choose to start with two identical pure astigmatism wave plates that totally cancel each other instead of reinforcing each other as in the example above. The identical plates are rotated relative to each other by 90 degrees:

$$Z(2,+2,\theta)+Z(2,+2,\theta+/-90)=Z(2,+2,\theta)-Z(2,+2,\theta) \quad (5)$$

This is identical to zero at any θ. The amplitude of the two wave plates are counter-rotated by angle φ:

$$Z(2,+2,\theta+\varphi)+Z(2,+2,\theta-\varphi) = -2\sin(2\theta)\sin(2\varphi) \quad (6)$$

$$= -2Z(2,-2,\theta)\sin(2\varphi) \quad (7)$$

In this case, the maximum amplitude of pure astigmatism is obtainable when counter rotational angle φ is at 45 degrees, or when the two plates are 90 degrees relative to each other. The maximum amplitude is achieved at counter rotational angle φ at 45 degrees where the amplitude of the ACA is the sum of the two wave plates. However, the resultant wave plate has wavefront profile of Z(2,−2) even though one starts out with two identical Z(2,2) plates. What this means is that variable amplitude pure astigmatism may be aligned along −45 degree angle relative to the starting orientation axis direction as defined by the two identical wave plates. This can be made understood using Equation (2) with Equation (7). Therefore, the power or the amplitude of the astigmatism is adjustable by controlling an angle between the axes of the two astigmatism wave plates. In a preferred embodiment, the negative cylinder axis of the Z(2,−2) is to be marked as the optical axis of the combined wave plate unit. In application, if the two starting wave plates were aligned to produce a net astigmatism of zero, or plano, as shown in Equation (5), after a counter rotation φ of the combined unit, the net optical axis of the astigmatism is at 45 degrees. It will produce a negative cylinder lens effect upon adding a negative power sphere lens at half of the astigmatism amplitude to the combined wave plate unit. When referring to an increase of astigmatism amplitude, one may achieve it by increasing the angle φ, so that a negative cylinder condition of an eye is reduced or neutralized. As an example, a negative cylinder notation with axis at zero degrees can be produced with a wave plate having a wavefront correction profile of −Z(2,2,θ) plus an appropriate amount of negative power sphere Z(2,0).

The present refraction method and device may include multiple or a series of cylindrical lenses in smaller diopter power increments to be inserted in place of the ACA to accomplish the advantageous objective of finding the optimal refraction for the patient. For example, an instrument including lenses in 0.125 diopters increments, or in 0.0625 diopter increments may be used.

Sign Convention for the Cylinder Lenses

A final prescription generated based upon the exemplary refraction procedure preferably has a minus cylinder notation. A negative cylinder notation may be converted to a plus cylinder notation in a spectacle prescription, which indeed specifies the same eyeglasses therefore, produces the same effects for refractive error correction. The instructions as described hereunder can be modified to arrive at a positive cylinder prescription. In that event, instead of finding the end point at a negative cylinder focal plane where the plane wave has an image of a sharp line, one would search for a sharp line image at the positive cylinder focal plane. One would also make corresponding modifications in the refraction procedure to accomplish the respective goals.

Electrical, Electronics Hardware and Computer Programs

Figure 5:
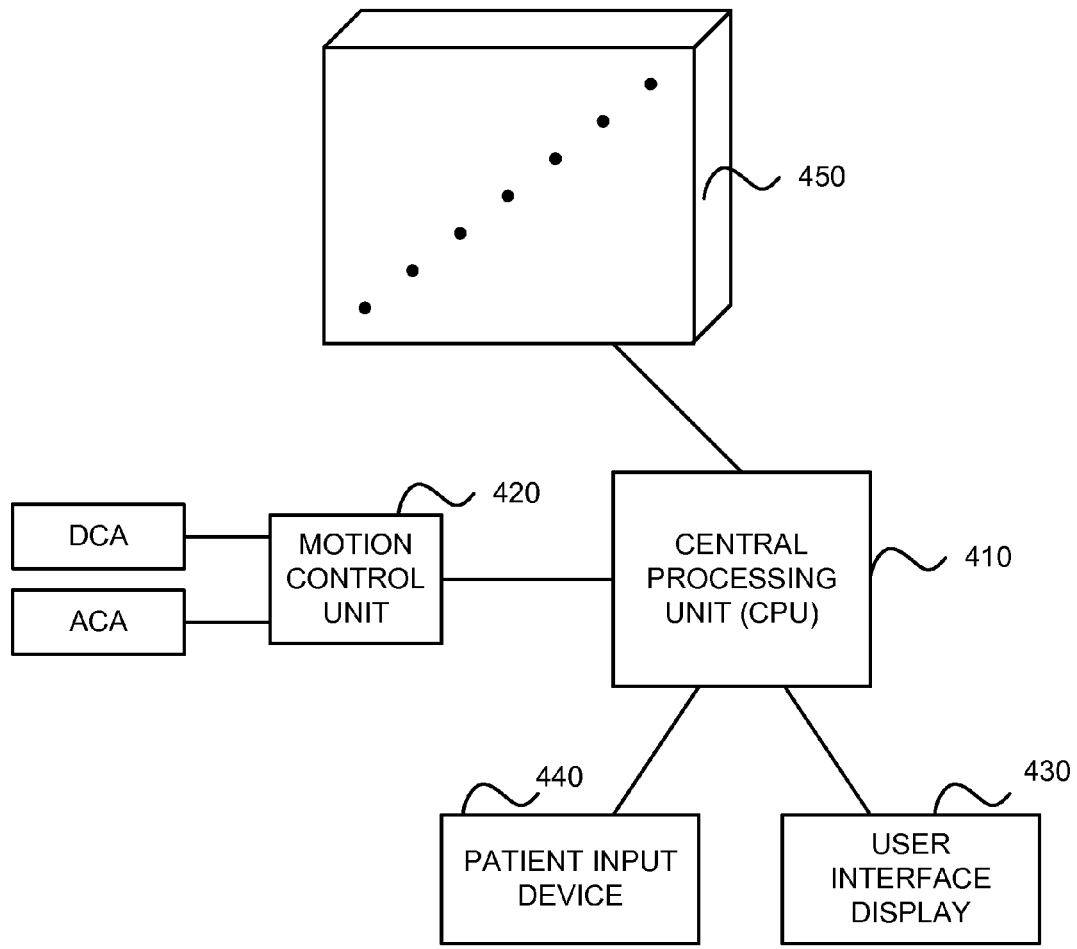
FIG. 5 illustrates a subjective refraction apparatus with electronic and/or software controls in accordance with an embodiment.
Figure 6A:
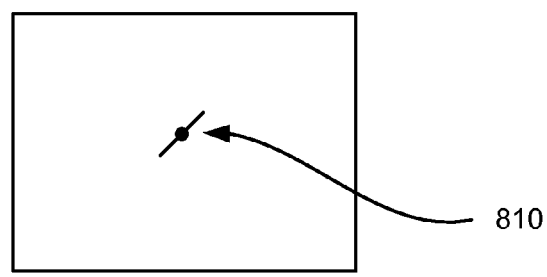
FIG. 6A illustrates a point with a small line through it representing a linear image appearing to a patient as adjusted from an initially blurry image of the point light source in accordance with an embodiment.
Figure 6B:
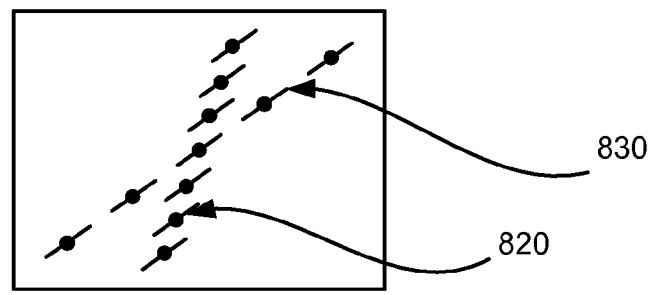
FIG. 6B illustrates a series of small line images arranged in a pair of crossed lines around an image of the point light source in accordance with an embodiment.
Figure 6C:
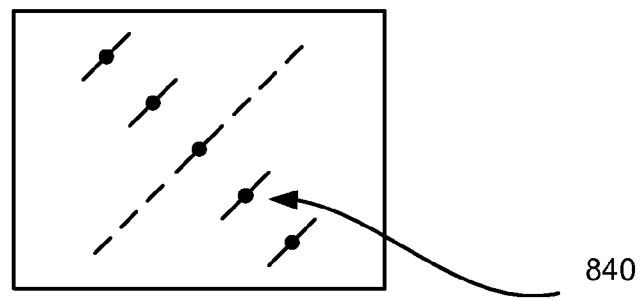
FIG. 6C illustrates a series of small line images arranged in a line and crossed with another line in accordance with an embodiment.
Figure 6D:
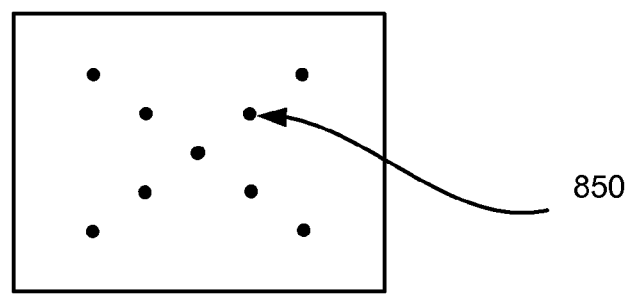
FIG. 6D illustrates two series of point images arranged in two crossed lines in accordance with an embodiment.
Figure 6E:
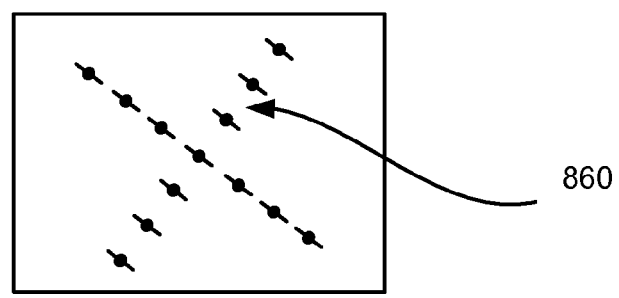
FIG. 6E illustrates a two series of short lines arranged in two crossed lines in accordance with an embodiment.

While the DCA and the ACA units can be adjusted manually, it is much more time efficient to have electrical and electronic hardware that connects a patient's input device such as push buttons and motors that move optical elements in the DCA and ACA, and/or use software to control the orientation of the sweep line or the generation of rings of various diameters at the QVM. These hardware and software components of an exemplary system are illustrated in FIG. 5. They preferably perform one or more of the following tasks.

A Motion Control Unit 420 may include a current amplifier and embedded electronics to direct the motion of the motors. It can drive the movement of one or more optical elements in the DCA, and/or ACA to change the defocus and/or astigmatism power and/or axis angle. It may also monitor the positional signal of the encoders at the DCA and/or ACA A User Interface Display 430 may include a display monitor, with or without touch screen capability. It displays the locations of the optical elements. The location information is to be obtained from an encoder attached to monitor the movement of lens 220, and likewise encoders for each of the rotary astigmatism plates at 310 and 320. It also displays a list of refraction procedure options such as optimizing defocus, astigmatism and/or locating the axis angle of the cylinder. It may also store and display an old prescription of a patient's eyeglasses or contact lenses, and/or those obtained with an autorefractor. By a touch of the screen or a clicking of a mouse, the DCA and/or ACA can be made to move to a pre-set prescription settings. These set locations may include a newly obtained, optimized prescription, an old eyeglasses prescription, or an autorefractor prescription. In this way, the patient can efficiently view and compare the quality of vision of two or more different prescriptions, thus advantageously adding another subjective or objective prescription component to the technique.

The Target 110, preferably a point source, can be generated on a computer monitor. The spot size, the display duration and its brightness may be controlled with computer software and/or a separate input device and/or monitor hardware control.

Items displayed at the QVM Monitor 450 may include multiple point sources, a line or multiple lines, multiple points on a line or on multiple lines. The displayed items may be programmed using software.

A Patient Input Device 440 can be joystick, a mouse, button, keyboard or keypad, voice-actuation, or a knob, or combinations thereof. The patient responds by clicking, pushing a button or turning a knob using hand or foot or other movement, or speaking a command such as start and/or stop, at the appropriate moment, to indicate the finding of a certain endpoint, while the DCA and ACA positions are being scanned and while he/she is viewing the displayed items at the target 110, or other displayed items 122, 124, 126, 128 130 or combination thereof. A patient can also push a button, etc., to start to move an optic and stop pushing the button to stop movement of the object, thus affirmatively stopping movement of the optic by ceasing to move it.

A Central Processing Unit (CPU) 410 includes a computing processor. The unit stores motion control commands and other programmed subroutines to perform refraction procedures. It also presents graphics and items to be displayed at the target monitor 450. The CPU may perform any or all of the following tasks:

Collect and send data from and among a Patient Input Device, User Interface Display, QVM monitor, the Motion Control Unit, then to DCA and ACA units;
  Convert location readings at the DCA and ACA to refractive powers in units of diopters. This can be accomplished with a software subroutine that has stored calibration information that relates position data to diopter powers;
  Adjust the intensity of the point source by controlling the current to the light source or actuator that inserts and removes neutral density filters in and out of the beam path, while alternatively, if the point sources are from the QVM monitor, its intensity and size can be adjusted through programming.
  Start and stop a sweeping motion of a sweep line using touch keys that electrically connect to the rotary drive mechanism of the sweep line. If the sweep line is generated on a QVM monitor, the sweep line or multiple point sources forming the line can be generated in a program.
  Link to input/output ports, upload or download programs to an embedded processors;
  Generate sweep line, parallel lines and/or rings or multiple points forming such patterns and at predetermined diameter or lengths at the QVM monitor;
  Adjust the orientation of the sweep line, preferably in multiple speeds, e.g., a high speed mode and a high resolution, slow scan mode;
  Set limits of travel range for the optics to avoid overcorrection;
  Automatically advance or decrease the DCA or ACA refractive power when such task is requested in a refraction procedure.

In FIG. 5, link and interaction among the various system components are indicated by connecting lines. That configuration is exemplary rather than limiting. For example, the Patient Input Device 440 may be linked to the Motion Control Unit 420, and the input signals from the patient can be routed through the Motion Control Unit 420 to the Central Processing Unit 410.

A Method of Wavefront Refraction Correcting Low Order Aberrations

A new refraction method is presented in the following. This method substantially differs from the current phoropter refraction method or auto-refractor refraction. The method may utilize the structural components described above with reference to FIGS. 1(a)-1(d) and 5, or other suitable configurations.

Figure 2:
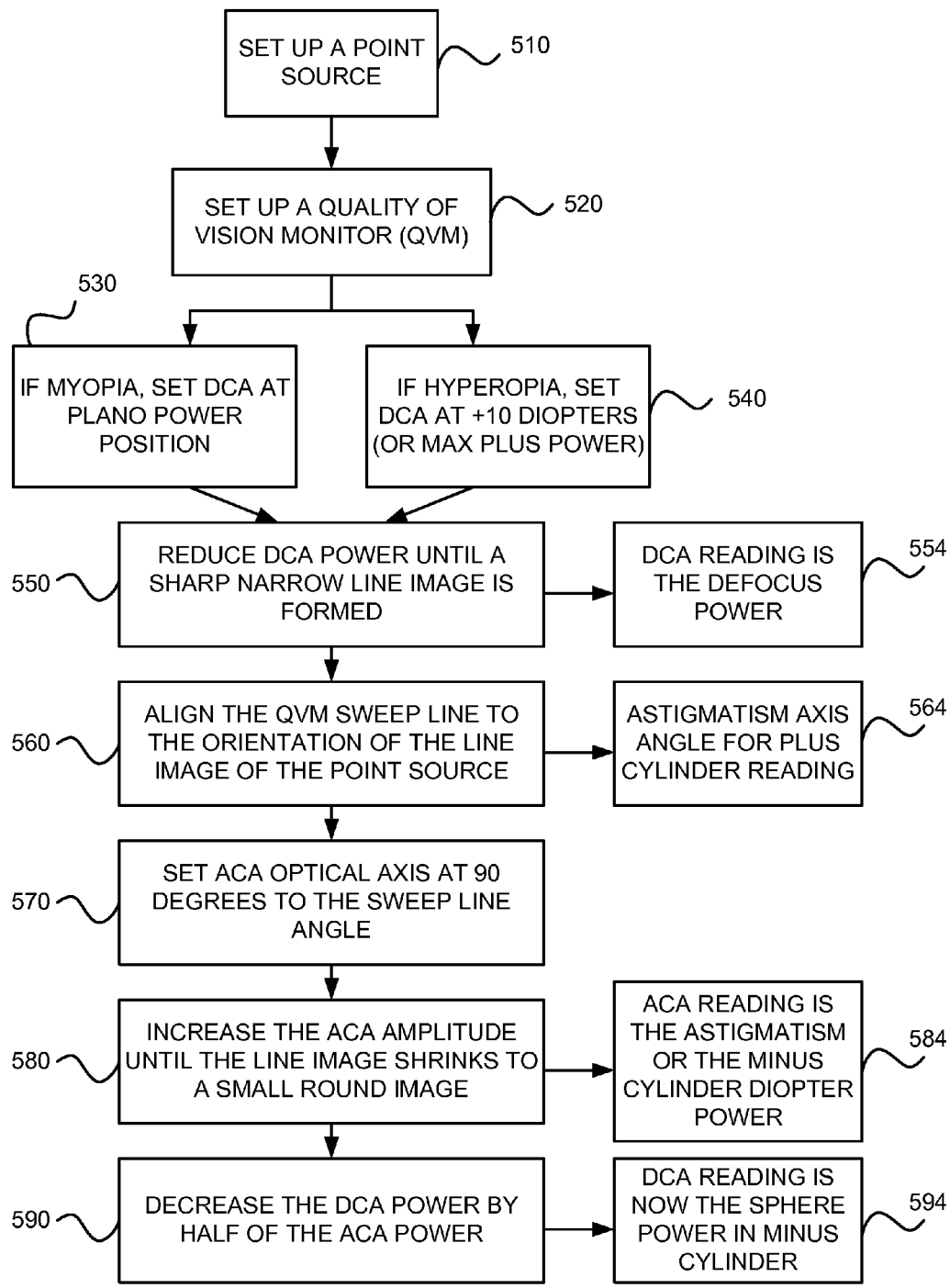
FIG. 2 is a flow chart illustrating a subjective refraction method in accordance with an embodiment.

First, in FIG. 2, Box 510, a point source is set up to generate substantially plane wavefronts and is used as a viewing target, instead of a Snellen chart or a Landolt-C chart, or another eye chart.

At or near the spectacle plane 400 of a patient's eye, an Astigmatism Corrector Assembly (ACA) 300 is placed. Following after the astigmatism corrector, a Defocus Corrector Assembly 200 is preferably placed. Other optical arrangement may be understood by those skilled in the art to achieve the objectives illustrated at FIGS. 8A-8G, i.e., to adjust an image of a point light source from having spherical, astigmatic and/or higher order aberrations to substantially a sharp image of the point light source. A Quality of Vision Marker (QVM) may be generated, e.g., on a LCD monitor. The location, structure and function of these components have been described earlier.

Wavefront Refraction Method

Figure 3:
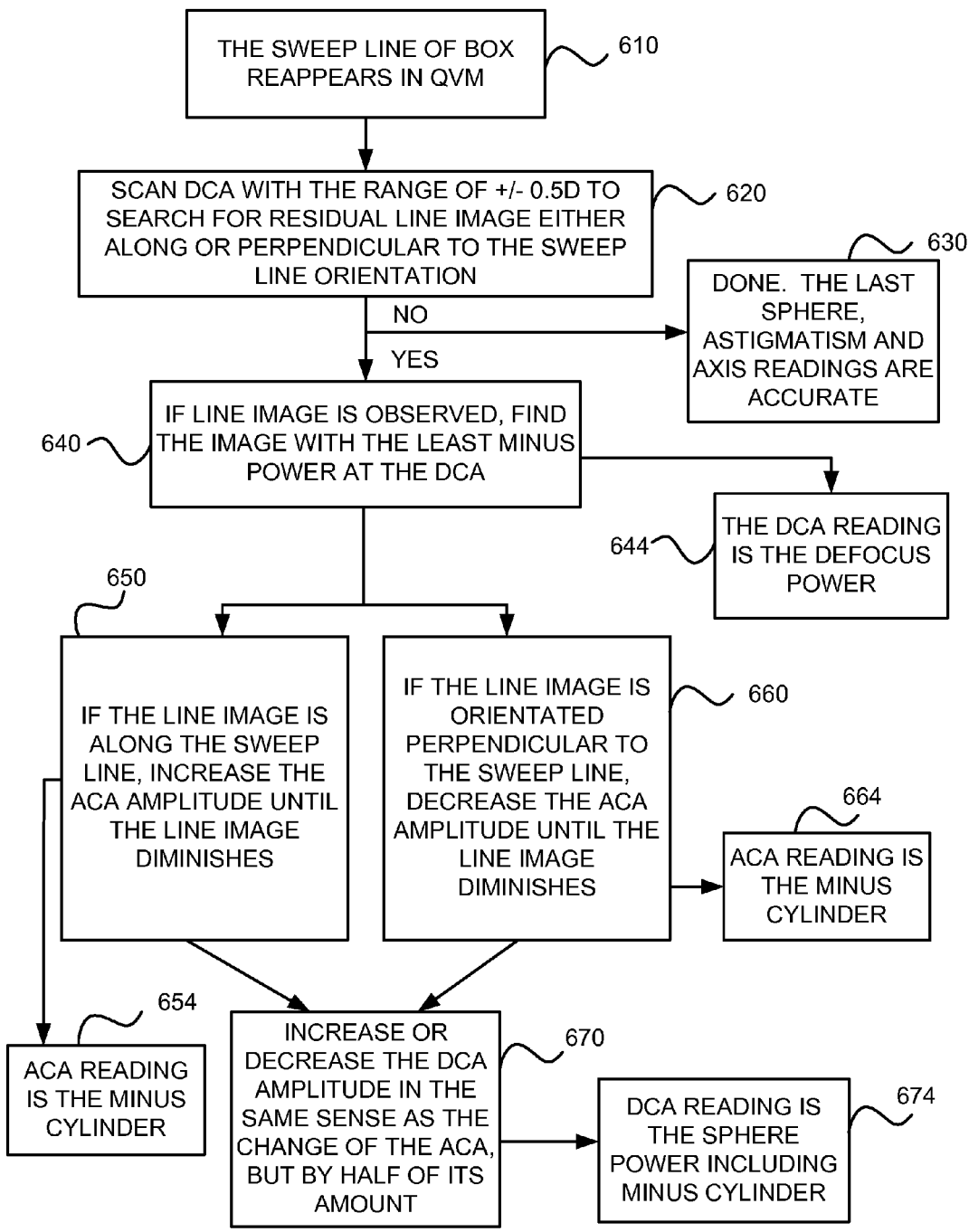
FIG. 3 is a flow chart illustrating a fine tuning of a subjective refraction method in accordance with an embodiment.

What follows is an exemplary embodiment of a wavefront refraction method for arriving at a spectacle prescription for a patient. Referring to FIGS. 1(a), 2 and 3:

1. Patient is seated in front of this refractor according to the FIG. 1(a) setup. Head is placed against the headrest, and eye looks directly at the point source, which is set up at about 6 meters away from the patient, Box 510. Preferably the source is placed at a perceivable distance of 2 meters or more away from the patient's eye. Due to the small dimension of the point source, the wavefront generated at the "point" at 2 meters or farther away over an entrance pupil of a patient is considered substantially collimated, and it approximates a plane wave wavefront. The patient is instructed to look directly at the collimated wavefront, which is either from an actual point source or from a laser as described earlier. When a point source is referred to herein, it is meant as either an actual point source, or an apparent image of a collimated wavefront from a laser source. A QVM is also preferably set up, and placed by the point source, or overlapping with the image of the point source via a partially transmitting, 45 degrees mirror, Box 530 as previously described.
2. If the patient has refractive errors, he/she would see a diffused light pattern rather than a sharp point image.
3. Both the astigmatism corrector and the defocus corrector may be first set at its zero power, or at its plano position.
4. If one knows the old spectacle prescription, the defocus corrector may be optionally set to the sphere value of the old eyeglasses plus 2 diopters, and this may be used as the starting point.
5. If one starts the refraction process from scratch, he or she may first press a switch that increases the defocus power in the DCA to high plus power.
6. (For hyperopic patients, skip to step 8). In Box 530, a myopia patient would see a more defused light patch, or a worse condition than with the spectacles. In Box 550, a patient is instructed to press the decrease diopter power switch for the DCA. The defocus corrector starts to move towards more negative power, and the defused image begins to improve, namely, the diffused light patch begins to collapse into a shape of a line, and the line image becomes more focused and preferably forms a sharp line or the patient indicates when the sharpest line is formed. The initially blurry image of the point light source, e.g., as illustrated at FIG. 8A, may be converged to a more linear shape, e.g., as illustrated at FIG. 8B, and to an optimally sharp line, e.g., as illustrated at FIG. 8C.

7. The patient is instructed to find the first appearance of an end point that the shape of the image of the plane wave is at its sharpest line image, and at the same time, the line image is at its longest length. This is an easily distinguishable end point, since most people can determine sharpness and length. Furthermore, the sharpness of a single line is easier to determine than the sharpness of entire letter sets when a Snellen chart is used in a phoropter refraction. The reading at the DCA at this point is the defocus power of the patient's refractive error, in Box 554. For myopia patients, skip to step 9.

8. For hyperopic patients, in Box 540, the patient will see an improvement as the defocus corrector increases in power from the plano position. He or she will experience the formation of a sharp line image as well. However, the patient is instructed to continue to press the increased defocus power button for the DCA, and told to expect the line image will get worse after it passes the sharp line image position. Then a second sharp line image position will come along. The patient is instructed to let that pass as well, but pause the image as he or she sees a fairly diffused line image. The objective here is to have the DCA at a power position more plus than the patient's hyperopia condition. The DCA may stop the DCA scan after the patient has seen the second sharp line image, or continue to scan all the way to +10 diopters, or the maximum plus power. In Box 550, now the decrease power button is tapped to move the line image gradually to find the first sharp line image that comes to view, and then stop. The reading at the DCA at this point is the defocus power of the patient's refractive error, Box 554.

9. After the objective of finding the narrowest line image with the longest line is accomplished, in Box 560, a radial sweep line is generated at the QVM monitor by a computer program. The intensity of the sweep is properly adjusted not to dominate or wash out the line image.

10. As soon as the line sweep is near or on top of the line image of the point source, the patient is instructed to press a stop button to stop the sweeping scan of the radial line generated at the QVM monitor. The patient then uses a fine stepping control button to move the sweep line either forward or reverse, to get a perfect overlap. The overlap position is preferably where the line sweep image appears to be the sharpest and narrowest to the patient. This is the axis angle at 90 degrees to (or perpendicular to) the minus cylinder axis of the patient's refractive error, in Box 564.

11. As an option, a method is provided to estimate the amplitude of the astigmatism. Two lines are generated from the sweep line position, and the sweep line from step 10 above vanishes as the two lines begin to separate and move apart in the direction perpendicular to the orientation of the sweep line. The patient is instructed to press a stop button, as the two lines are separate as much as the length of the sharp line image from the point light source. Again two push buttons are provided: one to increase, and the other to decrease, the separation distance of the two lines in small steps. When the separation distance is the same as the sharp line image length, a patient presses an accept button to take this astigmatism value. The amplitude of the line image of the point source is correlated to the astigmatism error. It is a function of the pupil diameter, (or the projection of the pupil shape along the astigmatism axis, if it is oval in shape) and the magnitude of the cylindrical error. The pupil diameter determines the cone angle of the focusing ray inside the eye, and the cylindrical error determines how much the beam is defocused before it reaches the focusing point of the astigmatism component. The defocus value of the eye, and the axial length of the eye are included in the calculation for an estimate of the amplitude of the astigmatism.

12. Now, one can use this amplitude as a first estimate of the cylinder, and apply this cylinder value to the astigmatism corrector with the axis angle set at exactly 90 degrees to the angle of the sweep line, and at the same time the defocus corrector decreases the power by a factor of two to move the minimum position, or the beam waist inside the eye to the retinal plane. The line image now collapses preferably into a small round shape, which is almost at its tightest focus point shape as indicated by the patient. The linear image, e.g., as illustrated at FIG. 8B or 8C, formed by the adjusting described at point 6 and/or at points 6-7 or 6-8 above, is then reduced in its long dimension to form a round or oblong shape, e.g., as illustrated at FIGS. 8D-8E, and/or as illustrated at FIGS. 8F-8G depending on whether fine-tuning and/or correction for higher order aberrations is needed and/or performed.

13. Alternative to steps 11 and 12, the astigmatism amplitude can be determined from scratch, namely without using any assumed estimates. In Box 570, either manually, or via electronics and a computer program, the optical axis of the Astigmatism Corrector Assembly (ACA) is moved to exactly 90 degrees from the angle of the sweep line. Box 580, the patient is instructed to push a control button that increases the amplitude of the astigmatism correction. The patient is instructed to stop increasing the value of the ACA, as soon as the line image has become round. In Box, 584, the ACA reading is the astigmatism or the minus cylinder power of the patient's refractive error. Box 590, the computer control receives the amplitude data from the ACA unit, and sends a sign to DCA unit to decrease the defocus power by an amount that is exactly half of the astigmatism amplitude. The round light image shrinks to a sharper focus spot. The DCA reading is the sphere component of the patient's refractive error, Box 594. At this point the spectacle prescription is achieved as shown in Boxes 564, 584, and 594.

14. Next and optionally, FIG. 3 is referred to Box 610. One may fine-tune the process to find an even more accurate spectacle prescription for the eye. First, the sweep line at its final accepted position reappears on the QVM monitor. In Box 620, the patient is asked to slowly increase and decrease the defocus power by tapping the increase and decrease buttons. In Box 630, if there is no residual sharp line image along the final sweep line axial orientation (a similar sharp focused line as seen in step 7 or 8, except shorter in length), nor any line image along 90 degrees from the sweep line angle, the astigmatism value is deemed to be correct, and no fine-tuning is determined.

15. In Box 640, if there are residual line images, one line along and one perpendicular to the sweep line orientation are expected. The patient is instructed to find these two image positions, while tuning the DCA power and identifying the one with the least minus power at the DCA. In Box 650, if the line image is along the sweep line angle, the ACA amplitude is increased (or more minus cylinder, the optical axis of the ACA being defined to provide minus cylinder power) to cancel this image. However, if the line image appears to be at a 90 degree (perpendicular to) the sweep line angle, in Box 660, the patient decreases the astigmatism amplitude at the ACA, until the line is minimized, and an accurate value for the astigmatism is achieved. The ACA reading is the minus cylinder power of the patient's refractive error, in Box 654 or Box 664.

16. Now, in Box 670, the computer/electronics control that drives the DCA either to increase or decrease the power by exactly half of the amplitude value of the astigmatism, corresponding to either an increase or a decrease of the ACA during the fine-tuning process. For example, if the patient needs more negative amplitude at the ACA in the last step, then the DCA power would also move to more minus, and vise versa. Here the more accurate value of the sphere power amplitude reading from the DCA is achieved, in Box 674.

For regular refraction, namely, one that corrects the sphere and cylinder and axis errors, the process is complete at step 16. This level of vision correction is denoted as point-source refraction. The final prescriptions are shown in Boxes 654 or 664 for the cylinder value, and 674 for the sphere. The axis value is unchanged as in Box 564/570,

Subjective Wavefront Refraction for Correcting Higher Order Aberrations

More often than not, there are higher order aberrations in the eye in addition to the sphere cylinder and axis errors. These higher order aberrations manifest themselves as starbursts, halos, or glares, especially during nighttime. Williams, Applegate and Thibos have been trying to use various theoretical models based mostly on optimization of certain metrics, which are assumed to be relevant to the quality of vision. They have arrived at over thirty such metrics, all of which have correlation to the quality of vision. The difficulty is to determine which one or which combination of many and their respective weight factors that ultimately predict the best spectacle correction. Instead of modeling, here a subjective method that allows the patient to actually find the best sphere, astigmatism and axis angle that also reduces the starburst effect of the higher order aberrations in the eye.

If one performs the method as stated above from step 1 to step 16, or uses existing prescription eyeglasses, and the patient still observes structures around the bright point source, which are results of higher order aberrations, and the patient desires to have such light rays reduced, the following refractive method will further improve the spectacle refraction by applying the low order components of defocus and astigmatism to correct the higher order aberrations. A preferred method of performing subjective wavefront refraction is provided.

Subjective Refraction Procedures that Reduce Higher Order Aberration Errors

One method of correcting higher order aberration errors is to construct a wavefront that is opposite to the aberration error, accomplishing cancellation. One such method is accomplished by producing a spatial optical path difference in a material medium, such as a polymer medium. Two commercial ventures have pursued correcting higher order aberrations using this approach. Calhoun Vision of Pasadena, Calif., developed light adjustable intraocular lenses that can in theory be used to correct higher order errors. Ophthonix, Inc. of San Diego, developed eyeglasses that incorporate a higher order cancellation profile by inducing an index of refraction change, hence an OPD profile in the lens material. Both approaches have the disadvantage of inducing worse higher order aberration, if the correction profile is misaligned with the aberration of the eye. In the case of Calhoun Vision, the profile is imprinted after the lens is implanted. However, misalignment during the writing process can occur and remains a problem. In the case of Ophthonix, eye movement when looking at various glaze angles can be detrimental to the correcting method. Hence a method that corrects part or all of the higher order aberrations, and does not induce a worsening in quality of vision is desirable.

Performing steps 1 through 16 under the regular refraction as described in previous paragraphs provides a good illustrative refraction prescription. This level of correction is referred to as Point Source refraction Rx, or Rx refraction in the following, and the defocus and astigmatism and axis angle as the Rx values.

In the following, a method of further improving the quality of vision is provided for reducing higher order aberrations, which results in less starburst or less radiating rays, and achieves a sharper vision. This is achieved by fine-tuning the defocus and the astigmatism, and allowing the freedom of change in all three components, the defocus, and astigmatism and the axis angle to achieve the effect of increasing the cancellation of the higher order aberrations using the second order terms of the Zernike polynomials. This method of correcting higher order using the second order terms of defocus and pure astigmatism permit some misalignment of the eyeglass optics with the eye's aberration profile, while the patient can still enjoy improved vision without the drawbacks of higher distortions when looking through various glazing angles.

Figure 4:
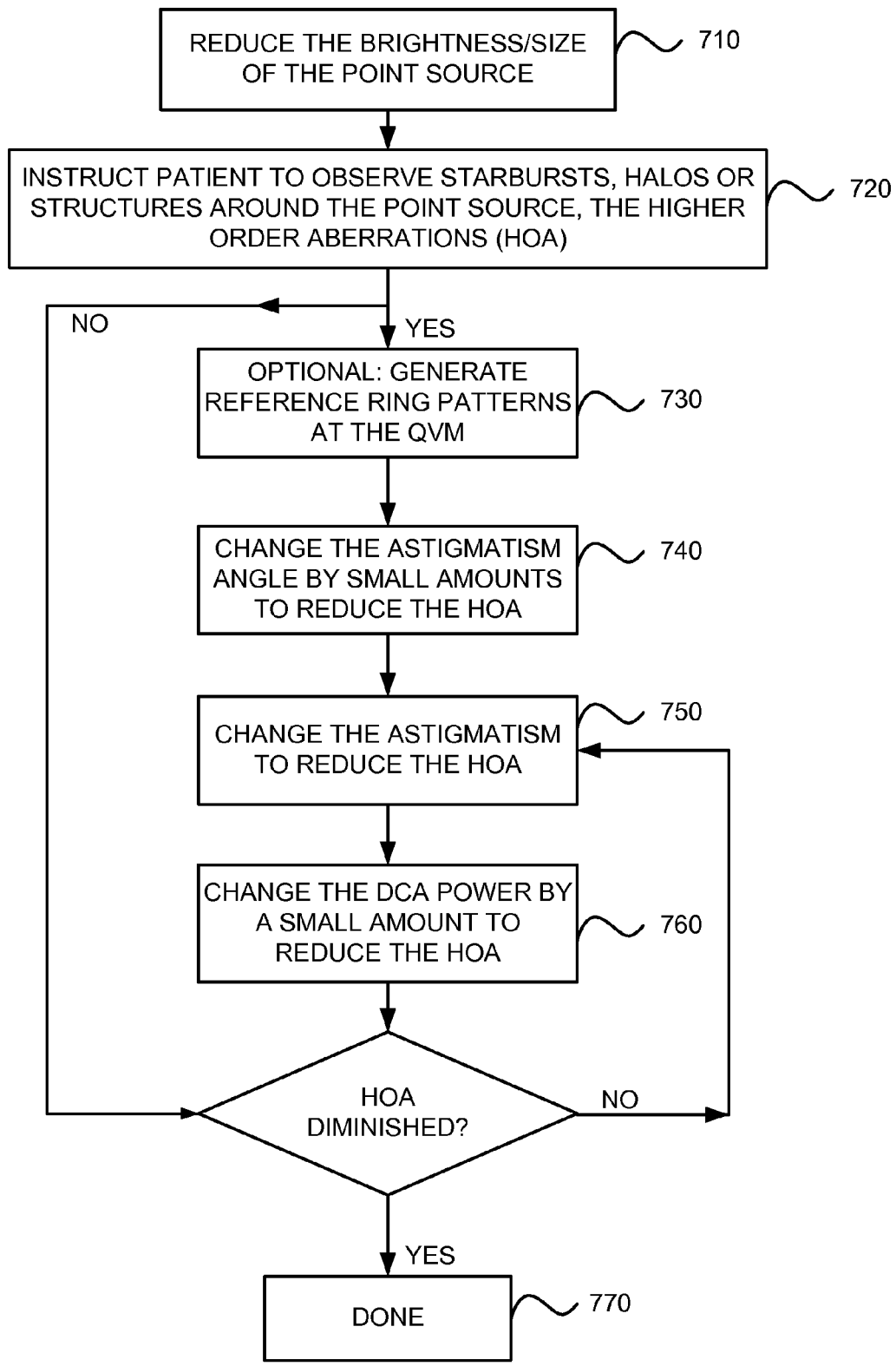
FIG. 4 is a flow chart illustrating correction of high order aberrations in accordance with an embodiment.

Referring to FIG. 4:

1. In Box 710, the brightness of the point source is reduced either using a neutral density filter, or reducing the light source current, or by other means. The range of the reduction factor is between several tens and several thousands.
2. Under reduced intensity, the contrast at the central vision is no longer saturated, by the tightly focused therefore very bright light source. In Box 720, the patient is instructed to look for fine structures or the radiating rays around the point source that are associated with the HOA.
3. If none of the HOA features are visible to the patient, the process is completed and the arrow takes it to Box 770, finished.
4. Next, in Box 730, a ring pattern is generated at the QVM monitor to mark the extent of the starbursts, namely a ring that contains the lengths of visible bursts or rays. This ring marker is used as a reference marker to find improvement by reducing the length of the starbursts.
5. In Box 740, tune the optical axis of the astigmatism corrector ACA to find the best astigmatism and angle. Here the use of tilting the astigmatism component to induce a small amount of astigmatism to compensate the HOA is provided. Since it is expected that the amount is small compared to an average astigmatism of about one diopter or more, the angle of tilt is also small. One approach is to first change the cylinder axis slightly about its Rx axis value. In one embodiment, a method is introduced to avoid over correction or erroneous refraction, by limiting the adjustable range of the angle value. The method of limiting is based on the magnitude of the astigmatism value and combining with estimated higher order errors that can be corrected by the astigmatism component, and setting this astigmatism component to be about 0.25 diopters equivalent. As an example, one may set a limit of the astigmatism value at 0.25 D. This estimated limit value is denoted as $\Delta_{cyl}$, which is the estimated maximum contribution of the cylinder component that may effectively reduce the higher order aberrations. The angle range is set to be within the angle permitted by the angle subtended by the astigmatism amplitude $A_{cyl}$ in the Rx:

The range of adjustable Astigmatism angle=+/−arctan $(\Delta_{cyl}/A_{cyl})$.

In an example, the limiting range of adjustable astigmatism amplitude is set at +/−$\Delta_{cyl}$. The astigmatism and axis angle fine-tuning may go back and forth until the tightest spot is found for the point source image. The changes are small and often subtle, and the corresponding change in the astigmatism or the angle are also small, typically much smaller than the 0.25 diopters and the 5-degree increments that are the typical accuracy levels in current phoropter instruments. This illustrates an advantage of device in accordance with a preferred embodiment which provides a continuously adjustable defocus and astigmatism and angle axis adjustment. The defocus and astigmatism increments can be as small as the resolution of the positional encoder incorporated in the instrument, which can be smaller than 0.01 diopters in defocus and astigmatism and 0.1 degrees in the axis angle. As for the manufacturing of high precision optics, CNC is capable of positional accuracy of 40 nanometers, and plastics can be cut to sub-micron accuracy. Furthermore, the QVM monitor with the reference rings, and continuously adjustable in small increments are contributing factors that enable arriving at a least aberrated point image. Without the benefits of the QVM and the continuous changes provided by the device of the preferred embodiment, it is highly unlikely for a phoropter method to find a prescription that reduces sufficiently the higher order aberrations.

6. Next, in Box 750, the ACA amplitude is adjusted to minimize the HOA features. This step is to recover the amplitude loss of Rx astigmatism.
7. Next, in Box 760, the defocus component is adjusted to minimize the HOA features. Again one may set a limit on the range of the DCA adjustment to 10% of the DCA amplitude or 0.25 diopters, whichever is greater.
8. Every time the point image gets tighter and smaller, with shorter or less starburst rays, the patient may reduce a ring diameter to zero-in, to find the least aberration correctible by the second order Zernike components.
9. If one wishes to further refine the wavefront refraction to search for an even tighter spot, one may repeat steps 5 through 7 above.

Subtle changes in image of letters in an eye chart would be much more difficult to discern with other phoropter refraction methods than that of a point image.

An Automated Method of Finding an Optimized Corrective Lens Prescription

An automated refraction method is provided which has increased speed and user-friendliness of inventive device. The process aims to accomplish in stepwise manner reaching a number of end points leading to an optimized refraction correction within a predetermined accuracy level. The sphere, cylinder and axis values generated by the device and method may be used in a prescription for eyeglasses or other corrective lenses such as contact lenses or intraocular lenses. This subjective refraction correction may also be used to construct a corneal tissue ablation profile and to apply it in refractive laser surgery.

Figure 7:
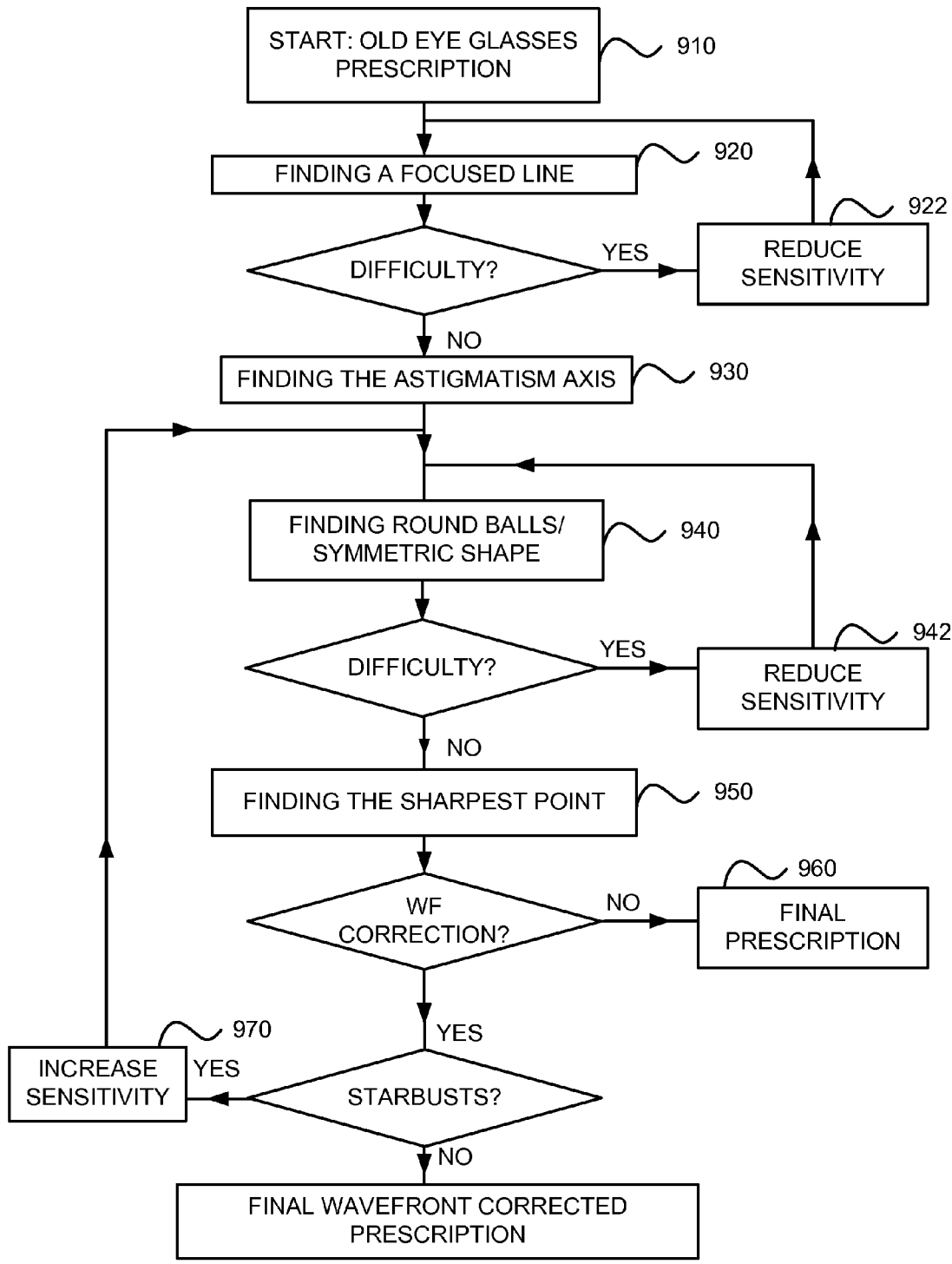
FIG. 7 is a flow chart illustrating a subjective refraction method in accordance with an embodiment.

The automated refraction process includes finding specific end points. Some details have been provided above and thus are incorporated and not otherwise repeated here. Referring now to FIGS. 6 and 7:

Step 1: Finding a Focused Line, Box 920

Using old eyeglasses or autorefractor values, or an arbitrary or average location, e.g., a 20/20 location, as the starting point at Box 910, the Central Processing Unit (CPU) sets a start and end position for the DCA. For example, the old eyeglasses prescription may be −2.75D, −1.50D at 120 degrees; again a negative cylinder convention is used in the example. The CPU will first set the scan range to +/−1.50D centering on −2.75D, and the step size at 0.5D. Therefore, the DCA will be set to scan from −1.25D to −3.25D in −0.5D steps to increasingly minus diopter powers.

The CPU presents in the QVM monitor a point source for the patient to view, including a number of pixels, at maximum brightness intensity. The cluster of pixels preferably forms a round shape that appears as a point at a sufficiently far distance.

The patient is ready to start, e.g., with an input device in hand. The CPU commences the scan to bring the "point source" stepwise to a more sharply focused line to the patient. The patient pushes a button or a trigger at the Patient Input Device (PID), to indicate the best image of a focused line has been reached as shown in FIG. 6(*a*), 810. The length of the line depends on the extent of the astigmatism in that patient. The patient may indicate an optimal image in other ways such as by releasing a button or verbal signaling or signaling an exam coordinator who then pushes a button or otherwise.

Next, a nesting method is used to pin point the optimized value at the DCA. Based on this patient input, the CPU set the scan range to +/−0.75D at the patient selected location at the DCA. For example, the patient picked −2.75 D. The new scan range is now −2.00D to −3.50D and the scan step size is reduced to −0.25D. This time, the patient selected −3.0D at the DCA. If a comparable refraction accuracy of a standard phoropter refraction procedure of 0.25 diopters is desired, one may stop here and record the sphere value for the patient. One may choose to continue to refine the accuracy to 0.125 D or even finer in a similar manner.

Each scan comprises of 7 presentation positions at the DCA. At one second per step of the presentation, the two scans will take about 15 seconds. One may skip the first scan of 0.5 D step if one is reasonably certain that the patient's refractive power has not changed beyond 0.75D.

Step 2: Finding the Astigmatism Axis Angle, Box 930

Again, one may use the axis angle from the old eyeglasses, CPU present a series of dots or multiple point sources forming a line, similar to the line pattern shown in FIG. 1 (*c*), except that the angle of rotation of the line relative to the center is set by the CPU to be at the old eyeglasses axis angle of 120 degrees. Now the patient sees a series of focused short lines, each centering at each of multiple points along a line pointing at 120 degrees. All angles are presented with the patient's perspective. The axis starts at the scientific minus x-axis. The doctor's perspective will convert that to positive x-axis.

Suppose that the actual cylinder axis of the patient is 135 degrees, not 120 degrees. Short focused lines at each of the dots will be pointing at 135 degrees, however, the center of the short lines are aligning along 120 degrees as shown in FIG. 6(*b*), 820. Patient is then instructed to rotate a knob in the PID to effect a rotation of the sweep line formed by a series of dots. When the direction of the line is aligned with the short line exhibited by the astigmatism of the patient's vision, the short lines overlap and form a "solid" line 830. Patient can easily fine tune the pointing direction by optimizing the "line" quality, with minimum or none of the short lines "sticking out" as shown in 830. Patient push a trigger to indicate the task done and the operator now marks the axis angle.

Note that the task of finding the angle of short line in FIG. 6(*a*) is made considerably easier by using a series of points and aligning them to the direction of the short line.

Moving the dotted line from 120 to 135 degrees by optimizing the quality of a line may take about 5 seconds.

Step 3: Finding Round Balls or Symmetric Shapes, Box 940

To neutralize the astigmatism errors, the patient is asked to turn the short lines into symmetrical or round light balls. CPU presents two cross lines of point or short line sources, as shown in FIG. 6(*c*). The two lines of points are pointing at 90 degrees cross, in one example, one line from the "Step 2" above, one line is pointing at 135 degrees (830) and one pointing at 45 degrees (840). At each point source, there is a short lines as in FIG. 6(*a*), 810, except now there are multiple points forming two cross lines, hence short lines arranged in a cross pattern.

The CPU uses the cylinder value of the old eyeglasses −1.50D as a starting point, and set the scan range to +/−0.75D in astigmatism diopter powers. In this example, it will cover from −0.75D to −2.25D in −0.25D steps. The method is analogous to those in "Step 1" above. Patient will see a shortening of the focused lines initially, until it turns into round, symmetric balls. If too much astigmatism is applied, short lines will begin to develop in the 90 degrees direction to the original short lines, in the example, the 135 degrees short lines (840) turn into short lines pointing to 45 degrees in FIG. 6(*e*), 860. This can be used as an indication that ACA is providing too much astigmatism correction. At the optimal point of this step 3, the image as perceived by the patient, are round balls (850) along the two cross lines in FIG. 6(*d*). At this juncture, patient confirms that the task is done, and the operator marks the astigmatism power. For example, the best astigmatism value may be at −1.25D.

The time to scan through the astigmatism is about 7 seconds. Therefore, the entire refraction process can be done in less than 60 seconds.

Step 4: Finding the Sharpest Point, Box 950

The CPU keeps the cross lines of round balls on the QVM monitor, or it may present just a single point as in FIG. 6(*a*) 810. The DCA is made to scan in −0.125D steps from the final position from Step 1. The patient is expected to pick a DCA value when he or she sees the sharpest point when it is first formed. It should be at around half of the astigmatism value which is −0.625D. To avoid over minus power, one may limit the maximum DCA move to no more than −0.5 D beyond the projected value of −3.625D. One may pick the less minus position selected by the patient under repeated scanning at the DCA. For example the final sharpest DCA value may be at −3.75D. Unless the patient wants to also correct the wavefront errors, the refraction procedure is completed and the optimized prescription for this patient is then Box 960 which may be −3.125D sphere, −1.25D cylinder at 135 degrees, in the example above.

Controlling the Sensitivity of the Test Procedure

In a subjective refraction, the outcome derives from a combination of the eye's optics, retina function, visual pathway and the interpretive power of the brain. Defects in any one of the components can degrade the quality of vision. The preferred technique identifies the optimized vision in a efficient manner.

In one embodiment, the sensitivity of the eye test is controlled by the size and the brightness of the point source. The larger the light spot or the "point source", the easier it is for the patient to identify end points. However, the larger the spot size, the worse is the spatial resolution and the attainable quality of vision. Therefore, an appropriate "point source" spot size is selected to attain a predetermined targeted level of quality of vision. One also controls the brightness of the presented point source to avoid saturation which may wash out details of starbursts and other features one may want to eliminate.

One may start with the assumption that 20/20 vision is achievable in a patient. One then sets the spot size to subtend a visual angle of 1 minute of arc. If the "point source" is placed at 6 meters from the patient, the object size is 1.75 mm for 1 minute of arc. One may use a slightly smaller spot size to account for diffraction and intensity saturation effects. For example, one selects a 1 mm diameter spot size point target at 6 meters for a 20/20 refraction.

If a patient undergoes the test through steps 1-4 above without too many repeated tests and delays, he or she is ready to move on to finding a better level of quality of vision. One may reduce the spot size to 0.5 mm at 6 meters for example and goes for the 20/10 vision.

On the other hand, a patient with cataract or macular degeneration conditions may have difficulty deciding the end points during the test steps 1-4, using a 1 mm target size and at 0.25D steps. One then increases the spot diameter to 1.5 or 2 mm or even larger until the patient can more easily identify the end points. When the spot diameter is increase to 2 mm or larger, the scan step size can also be increase from 0.25D to 0.5 D. The sensitivity reduction typically takes place at the Box 920 or Box 940. When the patient takes excessive amounts of time and/or cannot decide the end point after multiple presentations, the sensitivity is to be decreased, by increasing the spot size and increasing the step size as indicated in Box 922 and Box 942.

Correcting Higher Order Aberrations Using Automated Scanning Method

If the patient has healthy eyes, after standard phoropter refraction he or she still sees starbursts forming around a single point at QVM monitor as illustrated in FIG. 8F, and he or she desires to attain better vision, one needs to correct the higher order aberrations of the eye.

First, the Steps 1 through 4 above are to be completed and assume that patient shows no difficulty of finding all the end points. In Box 970, the operator increases the test sensitivity by reducing the spot size and the intensity of the light spot. If the items are displayed using the QVM monitor, the CPU, 510 can perform this task. The intensity is set such that the patient can see the starburst patterns around the point source and yet not too dim.

Next set the scan step size to 0.01D for both DCA and ACA. Move the sphere correction to the start position at +0.25D from the final prescription after the completion of Step 4 above. The scan range may be set at +/−0.25D. In our example, the start positions will be −2.875D and the ACA set at −1.00D and scan towards more minus powers.

Step 5: Finding the Most Symmetric Shape

Basically this step is repeating Step 3 above, using a finer step size of 0.01D for example and a smaller size target of 0.5 mm diameter, at non-saturating light intensity level. Patient use the input device to identify the location when the light source is most symmetrical or round. The scan may be repeated to check accuracy of the end point.

Step 6: Finding the Sharpest Point

After ACA scan is completed, scan the sphere power at DCA in 0.01D steps. Repeat the scan to check accuracy of the end point. Step 3A and 4A can be repeated until the patient confirms that starbursts have been substantially reduced or eliminated as illustrated in FIG. 8G.

The final prescription will be in the increments of 0.01 diopters in both sphere and cylinder. The axis angle may be in 0.5 degrees increments.

The present invention is not limited to the embodiments described above herein, which may be amended or modified without departing from the scope of the present invention as set forth in the appended claims, and structural and functional equivalents thereof.

In methods that may be performed according to preferred embodiments herein and that may have been described above and/or claimed below, the operations have been described in selected typographical sequences. However, the sequences have been selected and so ordered for typographical convenience and are not intended to imply any particular order for performing the operations.

In addition, all references cited above herein, in addition to the background and summary of the invention sections, are hereby incorporated by reference into the detailed description of the preferred embodiments as disclosing alternative embodiments and components.

I claim:

1. A subjective refraction method for generating a prescription for one or more corrective lenses for a patient, comprising:
   (a) disposing a patient's eye in a substantially fixed position;
   (b) displaying at least one item in a quality vision marker (QVM), and adjusting at least one of the display items relative to a linear image or a point image, or both, until an indication is provided by the patient;
   (c) forming a blurry image of the point light source at the patient's eye through an optical assembly, the image comprising a refractive error of sphere, astigmatism or higher order aberrations (HOA), or combinations thereof, of the patient's eye;
   (d) adjusting one or more optics of the optical assembly that are continuously disposed along an optical path between the point light source and the patient's eye,
   (e) searching until the patient indicates at least one of the following end points while looking at the item at the point light source:
      i) converging the blurry image to become a more linear image;
      ii) measuring the orientation of the linear image;
      iii) converging the linear image by reducing its long dimension; and
      iv) focusing the image substantially into a point-like image; and
   (f) determining a prescription for a corrective lens for the patient's eye based on known parameters of the optical assembly and on at least one adjusted position or orientation, or both, of the one or more optics of the optical assembly.

2. The subjective refraction method of claim 1, wherein the optical assembly comprises a defocus corrector assembly (DCA), and the adjusting comprises moving at least one lens of the DCA along the optical path until the patient indicates that the blurry image has become a linear image.

3. The subjective refraction method of claim 2, wherein the DCA comprises a pair of achromatic lenses disposed along the optical path including a fixed lens having a back focal length at a spectacle plane or equivalent spectacle plane of the patient's eye and a movable lens between the fixed lens and the point light source.

4. The subjective refraction method of claim 3, further comprising:
   (i) further adjusting a defocus power of the DCA within predetermined limits, including searching for a residual linear image of the point light source along the sweep line orientation;
   (ii) reducing the power of defocus corrector assembly to attain the least minus power and at which the patient indicates a sharper line image is formed at the point source; and
   (iii) increasing ACA power to reduce the linear image until the patient indicates a small and substantially round point image.

5. The subjective refraction method of claim 3, further comprising:
   (i) adjusting a defocus power of the DCA within predetermined limits, including searching for a residual linear image of the point light source perpendicular to the sweep line orientation;
   (ii) reducing the power of defocus corrector assembly to attain the least minus power and at which the patient indicates a sharper line image is formed at the point source; and
   (iii) decreasing ACA power to reduce the linear image until the patient indicates a small and substantially round point image.

6. The subjective refraction method of claim 1, wherein the optical assembly comprises a defocus corrector assembly (DCA), and the adjusting comprises inserting a lens of incremental defocus power in the optical path of the patient's eye.

7. The subjective refraction method of claim 6, further comprising:
   (i) further adjusting a defocus power of the DCA within predetermined limits, including searching for a residual linear image of the point light source along the sweep line orientation;
   (ii) reducing the power of defocus corrector assembly to attain the least minus power and at which the patient indicates a sharper line image is formed at the point source; and
   (iii) increasing ACA power to reduce the linear image until the patient indicates a small and substantially round point image.

8. The subjective refraction method of claim 6, further comprising:
   (i) adjusting a defocus power of the DCA within predetermined limits, including searching for a residual linear image of the point light source perpendicular to the sweep line orientation;
   (ii) reducing the power of defocus corrector assembly to attain the least minus power and at which the patient indicates a sharper line image is formed at the point source; and
   (iii) decreasing ACA power to reduce the linear image until the patient indicates a small and substantially round point image.

9. The subjective refraction method of claim 1, wherein the optical assembly further comprises an astigmatism corrector assembly (ACA), and the adjusting further comprises rotating at least one lens of the ACA until the patient indicates that the linear image has become a point image.

10. The subjective refraction method of claim 9, wherein the ACA comprises a pair of astigmatism wave plates disposed approximately at a spectacle plane or equivalent spectacle plane of the patient's eye.

11. The subjective refraction method of claim 1, wherein the optical assembly further comprises an astigmatism corrector assembly (ACA), and the adjusting further comprises inserting lens of incremental cylindrical power in the optical path of the patient's eye.

12. The subjective refraction method of claim 1, wherein the at least one display item comprises a sweep line, and the adjusting of the display item comprises overlapping the sweep line with the linear image until an indication by the patient, and using the orientation of the linear image to determine astigmatism axis angle.

13. One or more spectacle, contact or intraocular lenses having a prescription generated by the subjective refraction method of claim 1.

14. A subjective refraction method for adjusting a refractive correction prescription for a patient, comprising:
   providing at least one point light source outside of a patient's eye and an adjustable optical system for forming an initially blurry image of the point light source at the patient's eye, the image comprising a refractive error of sphere, astigmatism or higher order aberrations (HOA), or combinations thereof, of the patient's eye;
   while adjusting the optical system, searching until the patient indicates one or more end points while looking at the image of the point light source, including
      converging the blurry image into a substantially-condensed linear image; or
      measuring an orientation of the linear shape image; or
      converging the linear image or the blurry image into a round or best possible symmetric shape; or
      focusing the round image into a best possible focused point, or
      combinations thereof; and
   adjusting the prescription for correcting higher order aberrations (HOA), including:
      (i) selecting a brightness of the point light source; or
      (ii) selecting one or more physical dimensions of the point light source, or (iii) both (i) and (ii).

15. A subjective refraction method for adjusting a refractive correction prescription for a patient, comprising:
   providing at least one point light source outside of a patient's eye and an adjustable optical system for forming an initially blurry image of the point light source at the patient's eye, the image comprising a refractive error of sphere, astigmatism or higher order aberrations (HOA), or combinations thereof, of the patient's eye;
   while adjusting the optical system, searching until the patient indicates one or more end points while looking at the image of the point light source, including searching until the patient indicates one or more end points including:
      (a) adjusting astigmatism correction amplitude to converge the blurry image into substantially a linear shape; or
      (b) adjusting defocus correction amplitude to reduce the long dimension of the linear shape or converge the linear shape into a best possible symmetric shape, or
      (c) both (a) and (b); and
   adjusting the prescription for correcting higher order aberrations (HOA), including:
      (i) selecting a brightness of the point light source; or
      (ii) selecting one or more physical dimensions of the point light source, or
      (iii) both (i) and (ii).

16. One or more spectacle, contact or intraocular lenses having a prescription generated by the subjective refraction method of claim 14.

17. One or more spectacle, contact or intraocular lenses having a prescription generated by the subjective refraction method of claim 15.

* * * * *